US008911761B2

(12) United States Patent
Knight

(10) Patent No.: US 8,911,761 B2
(45) Date of Patent: *Dec. 16, 2014

(54) COMPOSITE MATERIALS

(75) Inventor: David Philip Knight, Hampshire (GB)

(73) Assignee: Oxford Biomaterials Limited, Oxford (GB)

(*) Notice: Subject to any disclaimer, the term of this patent is extended or adjusted under 35 U.S.C. 154(b) by 1511 days.

This patent is subject to a terminal disclaimer.

(21) Appl. No.: 11/515,922

(22) Filed: Sep. 5, 2006

(65) Prior Publication Data

US 2007/0113355 A1 May 24, 2007
US 2012/0023677 A9 Feb. 2, 2012

Related U.S. Application Data

(63) Continuation of application No. PCT/EP2005/002473, filed on Mar. 4, 2005.

(30) Foreign Application Priority Data

Mar. 5, 2004 (GB) .................................. 0405045.6

(51) Int. Cl.
*A61F 2/00* (2006.01)
*C07K 14/435* (2006.01)
*A61L 27/48* (2006.01)

(52) U.S. Cl.
CPC ..... *C07K 14/43518* (2013.01); *C07K 14/43586* (2013.01); *A61L 27/48* (2013.01)
USPC ........................................................ 424/423

(58) Field of Classification Search
None
See application file for complete search history.

(56) References Cited

U.S. PATENT DOCUMENTS

| 4,343,617 | A | * | 8/1982 | Baur, Jr. ........................ 8/127.6 |
| 4,818,291 | A | | 4/1989 | Iwatsuki et al. |
| 4,963,146 | A | | 10/1990 | Li |
| 5,019,087 | A | | 5/1991 | Nichols |
| 5,026,381 | A | | 6/1991 | Li |
| 5,245,012 | A | | 9/1993 | Lombari et al. |
| 5,656,605 | A | | 8/1997 | Hansson et al. |
| 5,834,029 | A | | 11/1998 | Bellamkonda et al. |
| 6,090,117 | A | | 7/2000 | Shimizu |
| 6,589,257 | B1 | | 7/2003 | Shimizu |
| 2002/0051806 | A1 | | 5/2002 | Mallapragada et al. |
| 2003/0028204 | A1 | | 2/2003 | Li et al. |
| 2003/0100108 | A1 | | 5/2003 | Altman |
| 2004/0005363 | A1 | | 1/2004 | Tsukadas et al. |
| 2004/0170827 | A1 | * | 9/2004 | Crighton ....................... 428/357 |
| 2004/0199241 | A1 | * | 10/2004 | Gravett et al. ................ 623/1.13 |
| 2005/0260706 | A1 | | 11/2005 | Kaplan et al. |

FOREIGN PATENT DOCUMENTS

| GB | 2386841 A | | 10/2003 |
| JP | 2004173772 A | | 6/2004 |
| WO | 94/22584 A1 | | 10/1994 |
| WO | 97/37002 A1 | | 10/1997 |
| WO | 98/22155 A1 | | 5/1998 |
| WO | 01/36814 A2 | | 5/2001 |
| WO | 01/38373 A1 | | 5/2001 |
| WO | 01/56626 A1 | | 8/2001 |
| WO | 02/081793 A1 | | 10/2002 |
| WO | 03/043486 A2 | | 5/2003 |
| WO | 04/000915 A2 | | 12/2003 |
| WO | 2004/016651 A2 | | 2/2004 |
| WO | 2004/060424 A2 | | 7/2004 |
| WO | 2005/094911 A2 | | 10/2005 |
| WO | 2006/030182 A2 | | 3/2006 |
| WO | WO 2006/030182 | * | 3/2006 |
| WO | 2006/108684 A1 | | 10/2006 |

OTHER PUBLICATIONS

Sezutsu et al., "Dynamic Rearrangement Within the *Antheraea pernyi* Silk Fibroin Gene Is Associated with Four Types of Repetitive Units" J. Mol. Evol., 2000, 51(4):329-338.*
TrEMBL information for Q81SB3, from < www.uniprot.org/jobs/201103291GCDTRR4BN.fasta >, Mar. 29, 2011.*
MedlinePlus Medical Encyclopedia—Anastomosis: <www.nlm.nih.gov/medlineplus/ency/article/002231.htm> retrieved Apr. 8, 2011.*
Li et al., "Compliant film of regenerated *Antheraea* pernyi silk fibroin by chemical crosslinking", Int. J. Biological Macromolecules, 2003, 32:15-163.*
Datta et al., "Differential expression of the fibroin gene in developmental stages of silkworm, *Antheraea mylitta* (Saturniidae)", Comparative Biochemistry and Physiology Part B 129, 2001, pp. 197-204.*
Sequence from *A. yamamai* silk fibroin Q964F4—deposited by Lee et al., Dec. 2001.*
Altman GH et al Biomaterials vol. 24: 401-16, 2003.
TrEMBL information for O76786, last modified Aug. 10, 2010, Version 31.
TrEMBL information for Q8ISB3, last modified Feb. 10, 2009, Version 18.
Minoura et al., "Attachment and Growth of Fibroblast Cells on Silk Fibroin", Biochem. & Biophys. Res. Comm., vol. 208, No. 2, Mar. 17, 1995, pp. 511-516.
Asakura et al., "Production and characterization of a silk-like hybrid protein, based on the polyalanine region of Samia *Cynthia ricini* silk fibroin and a cell adhesive region derived from fibronectin", Biomaterials, vol. 25, 2004, pp. 617-624 (abstract only).

* cited by examiner

*Primary Examiner* — Suzanne M Noakes
(74) *Attorney, Agent, or Firm* — Bacon & Thomas, PLLC

(57) ABSTRACT

This application discloses a composite material comprising one or more silk elements in an acrylic or cross-linked protein matrix. The silk elements are made from the group of silk elements consisting of domestic silkworm silk, wild silkworm silk, spider dragline silk, and filaments spun from recombinant silk protein or protein analogs. The composite material is particularly useful for use in-surgical-implants.

20 Claims, 7 Drawing Sheets

```
                    AGAAAGAAA                    SAARRAGHDSAAGSAAAAAAAAAAAAA
GSSARRGGGFYETHNSYSSYGSGSSSAAA                    SGAGGSGGGYGWGDGGYGSDSAAAAAAAAAAAAAA
         GSGAGGVGGGYGSDSAAAAAAAAAA               GSGAGGAGGGYGWGDGGYGSDSAAAAAAAAAAAAA
         SGAGGSGGYGGYGSDSAAAAAAAAAAAAA                 SGARGSGGYGGYGSDSAAAAAAAAAAAAA
         GSGAGGSGGYGGYGGYGSDSAAAAAAAAAAAAAA      GSGAGGVGGGYGWGDGGYGSDSAAAAAAAAAAAAA
         GSSAGGAGGGYGWDDGGYGSDSAAAAAAAAAAAAAA              GSGAGGRGDGGYGSGSSAAAAAAAAAA
         GSGAGGSGGYGGYGSDSAAAAAAAAAAAAA                    RRAGHDRAAGSAAAAAAAAAAAAA
         GSSAGGAGGGYGWDDGGYGSDSAAAAAAAAAAAAA     SGAGGSGGGYGWGDGGYGSDSAAAAAAAAAAAAAA
               SSGAGCRGDGGYGSGGSSAAAAAAAAAAAA    SGAGGSGGYGGYGSDSAAAAAAAAAAAAAA
                    RRAGHDRAAGSAAAAAAAAAAAAA     GSGAGGAGGGYGWGDSGYGSDSAAAAAAAAAAAAA
         SGAGGSGGGYGWGUGGYGSDSAAAAAAAAAAAAAA      SGAGGSGGYGGYGGYGSDSAAAAAAAAAAAAAA
         GSGAGGAGGGYGWGDGGYGSDSAAAAAAAAAAAAAA    GSGAGGAGGGYGWGDGGYGSDSAAAAAAAAAAAAA
         SGAGGSGGYGGYGSDSAAAAAAAAAAAAA                     GSGAGGRGDGGYGSGSSAAAAAAAAAAA
         GAGAGGAGGGYGWGDGGYGSDSAAAAAAAAAAAAA               RRAGHDRAAGSAAAAAAAAAAAAA
               GSGAGGRGDGGYGSGSSAAAAAAAAAAA     SGAGGSGGGYGWGDGGYGSDSAAAAAAAAAAAAAA
                    SAARRAGHDSAAGSAAAAAAAAAAAAA  SGAGGSGGYGGYGSDSAAAAAAAAAAAAAA
         SGAGGSGGGYGWGDGGYGSDSAAAAAAAAAAAAAA     GSGAGGAGGVYGWGDGGYGSDSAAAAAAAAAAAAA
         GSGAGGAGGGYGWGDGGYGSDSAAAAAAAAAAAAAA    SGAGGSGGYGGYGSDSAAAAAAAAAAAAA
               SGARGSGGYGGYGSDSAAAAAAAAAAAAA    SGAGGAGGYGGYGSDSAAAAAAAAAAAAA
         GSGAGGVGGGYGWGDGGYGSDSAAAAAAAAAAAAA              GSGAGGRGDGGYGSGSSAAAAAAAAAAA
               GSGAGGRGDGGYGSGSSAAAAAAAAAA                RRAGHDRAAGSAAAAAAAAAAAAA
                    SAARRAGHDSAAGSAAAAAAAAAAAAA  SGAGGSGGGYGWGDGGYGSSDSAAAAAAAAAAAAAA
         SGAGGSGGGYGWGDGGYGSDSAAAAAAAAAAAAAA     GSGAGGAGGAYGWGDDGYGSDSAAAAAAAAAAAAA
         GSGAGGAGGGYGWGDGGYGSDSAAAAAAAAAAAAAA    GSGAGGRGGAYGWGDGGYGSDSAAAAAAAAAAAAA
               SGARGSGGYGGYGSDSAAAAAAAAAAAAA              GSGAGGRGDGGYGSGSSAAAAAAAAAAA
         GSGAGGVGGGYGWGDGGYGSDSAAAAAAAAAAAAA              RRAGHDRAAGSAAA

```
SGAGGSGGYGGYGGYGGYGSDSAAAAAAAAAAAAAAA         GSGAGGRGDGGYGSGSSAAAAAAAAAAAA
GSGGGVGGGYGWGDGGYGSDSAAAAAAAAAAAA            RRAGHDHAAGSSGGGYSWDYSSYGSESAAAAAAAAAAA
GSGAGGRGDGGYGSGSSAAAAAAAAAAAA                GSGAGGVGGGYGGGDGGYGSGSSAAAAAAAAAAAAA
       RRAGHDRAAGSAAAAAAAAAAAAAA                     RRAGHDRAAGSAAAAAAAAAAAAAA
SGAGGAGGGYGWGDGGYGSDSAAAAAAAAAAAAA           SGAGGSGGGYGWGDGGYGSDSAAAAAAAAAAAAAA
GSGAGGAGGGYGWGDDGYGSDSAAAAAAAAAAAAAAA        GSGAGRAGGDYGWGDGGYGSDSAAAAAAAAAAAA
GSGAGGRGGGYGWGDGGYGSDSAAAAAAAAAAAAAAA        SGAGGSGGGYGWGDGGYGSDSAAAAAAAAAAA
       GSGAGGRGDGGYGSGSSAAAAAAAAAAAAAA       SGAGGSGGGYGWGDGGYGSDSAAAAAAAAAAAAA
       RRAGHDRAAGSAAAAAAAAAAAAAA                     GSGAGGRGDGGYGSGSSAAAAAAAAAAAA
SGAGGSGGYGGYGGYGSDSAAAAAAAAAAAAA                     RQAGHERAAGSAAAAAAAAAAAAAA
GSGAGGAGGYGGYGGYGSDSAAAAAAAAAAAAA            SGAGGSGRGYGWGDGGYGSDSAAAAAAAAAAAAAA
GSGAGGVGGGYGWGDGGYGSDSAAAAAAAAAAAAAAAA       GSGAGGAGGDYGWGDGGYGSDSAAAAAAAAAAA
       GSGAGGRGDGGYGSGSSAAAAAAAAAAAAA        SGAGGSGGGYGWGDGGYGSDSAAAAAAAAAAA
       RRAGHERAAGSAAAAAAAAAAAAAA                     GSGAGGRGDGGYGSGSSAAAAAAAAAAAAA
SGAGRSGGSYGWGDGGYGSDSAAAAAAAAAAAAAAA                 RRAGHDRAAGSAAAAAAAAAAAAAAA
SGAGGSGGYGGYGGYGSDSAAAAAAAAAAAAAA            SGAGGSGGGYGWGDGGYGSDSAAAAAAAAAAAAAAA
SGAGGAGGYGGYGGYGSYGSDSAAAAAAAAAAAAA          GSGAGGAGGDYGWGDGGYGSDSAAAAAAAAAAA
GSGAGGVGGGYGWGDGGYGSDSAAAAAAAAAAAAAA         SGAGGAGGGYGWGDGGYGSDSAAAAAAAAAAAAA
GSGAGGRRGYGAYGSDSSAAAAAAAAAAA                        GSGAGGRGDGGYGSGSSAAAAAAAAAAAAA
SGAGGSGGGYGWGDGGYGDSAAAAAAAAAAAAAAA                  RRAGHDRAAGSAAAAAAAAAAAAAAA
GSGAGGIGGGFQRGDGGYGSGSSAAAAAAAAAAAAA         SGAGGSGGGYGWGDGGYGSDSAAAAAAAAAAAAAAA
       RRAGHGRSAGSAAAAAAAAAAAAAAAA           GSGAGGAGGDYGWGDGGYGSDSAAAAAAAAAAA
SSGAGGSGGSYGWDYESYGSGSAAAAA                  SGAGGSGGGYGWGDGGYGSDSAAAAAAAAAAAAAA
GSGAGGSGGGYGWGDGGYGSGSSAAAAAAAAAAAAA                 GSGAGGRGDGGYGSGSSAAAAAAAAAAAAA
       GSRRSGHDRAYGAGSAAAAAAAAAAAAA                  RRAGHDRAAGSAAAAAAAAAAAAAAAA
GSSARGGSGFYETHDSYSSYGSGSSSAAAA               SGAGGSGGGYGWGDGGYGSDSAAAAAAAAAAAAAAAA
SSGAGGAGGGYGWGDGGYGSDSAAAAAAAAAAAAAA         GSGAGGAGGDYGWGDGGYGSDSAAAAAAAAAAAAA
```

FIG. 4B

```
SGAGGAGGGYGWGDGGYGSDSAAAAAAAAAAAAA      SGAGGAGGGYGWGDGGYGSDSAAAAAAAAAAAAA
     GSGAGGRGDGGYGSGSSAAAAAAAAAAAAA          GSGAGGRGDGGYGSGSSAAAAAAAAAAAAAA
         RRAGHDRAAGSAAAAAAAAAAAAAA                RRAGHDRAAGSAAAAAAAAAAAAAA
SGAGGSGGGYGWGDGGYGSDSAAAAAAAAAAAAA      SGAGGSGGGYGWGDGGYGSNAAAAAAAAAAAAA
GSGAGGVGGGYGWGDGGYGSDSAAAAAAAAAAAAA     GSGAGGVGGGYGWGDGGYGSDSAAAAAAAAAAAAA
     SGAGGAGGYGGYGSDSAAAAAAAAAAAAA      GSGAGGAGGGYGWGDGGYGSDSAAAAAAAAAAAA
SSGAGGAGGGYGWGDGGYGSDSAAAAAAAAAAAAA          GSGAGGRGDGGYGSGSSAAAAAAAAAAAAAA
     GSGAGGRGDGGYGSDSAAAAAAAAAAAAAA               RRAGHDRAAGSAAAAAAAAAAAAA
SGAGGSGGGYGWGDGGYGSDSAAAAAAAAAAAAA      SGAGGSGGGYGWGDGGYGSDSAAAAAAAAAAAAA
GSGAGGVGGGYGWGDGGYGSDSAAAAAAAAAAAAA     GSGAGGAGGDYGWGDGGYGSDSAAAAAAAAAAA
     SGAGGAGGYGGYGSDSAAAAAAAAAAAAA           SGAGGSGGYGGYGSDSAAAAAAAAAAAAAA
GSGAGGAGGGYGWGDGGYGSDSAAAAAAAAAAAAA     GSGAGGAGGDYGWGDGGYGSDSAAAAAAAAAAA
         SGAGGRGDGGYGSGSSAAAAAAAAAAAAA       SGAGGSGGYGGYGSDSAAAAAAAAAAAAAAA
         RRAGYDRAAGSAAAAAAAAAAAAAA      GSGAGGVGGGYGWGDGGYGGYGSDSAAAAAAAAAAA
SGAGGSGGGYGWGDGGYGSDSAAAAAAAAAAAAA          GSGAGGVGGGYGRGDSGYGSGSSAAAAAAAAAAAA
     SGAGGAGGGYGGYGSDSAAAAAAAAAAAAA              RRAGHDRSSGSAAAAAAAAAAAAAA
GSGAGGAGGGYGWGDGGYGSDSAAAAAAAAAAAAA     SGAGGSGGGYGWDYGSYGSDSAAAAAAAAAAAA
         SGAGGRGDGGYGSGSSAAAAAAAAAAAA   SSGAGGSGGGYGWDYGGYGSDSAAAAAAAAAAAA
         RRAGYDRAAGSAAAAAAAAAAAAAA      GSGAGGSGGGYGWGDGGYGSDSAAAAAAAAAAAA
SGAGGSGGGYGWGDGGYGSDSAAAAAAAAAAAAA           GSGAGGRGDGGYGSGSSAAAAAAAAAAAAAA
     SGAGGAGGGYGGYGSDSAAAAAAAAAAAAA     RRAGHDH

```
1-    29   (61.38/ 9.15)   AAAAA....aaA....AGSG..AG.GRGDGGYGSGS...S.AAA
56-   87   (70.28/12.52)   AAAAA..aasgA....GGSG..GGYGWGDGGYGSDS...A.AAA
130-  152  (56.50/ 7.31)   ...........A....GGAG..GGYGWGDGGYGSDS...A.AAA
153-  184  (61.11/ 9.05)   AAAAAaaaasgA....GGS...GGYG.GYGGYGSDS...A.AAA
219-  247  (61.38/ 9.15)   AAAAA......A..aaAGSG..AG.GRGDGGYGSGS...S.AAA
275-  306  (70.28/12.52)   AAAAA..aasgA....GGSG..GGYGWGDGGYGSDS...A.AAA
372-  400  (55.88/ 7.07)   AAAAA......A...aAASG.aGGSG.GYGGYGSDS...A.AAA
401-  430  (55.33/ 6.87)   AAAAA......A..aaAASG.aGGAG.GYGGYGSDS...A.AAA
466-  494  (57.38/ 7.64)   AAAAA.....aA....AGSG..AG.GRGDGGYGSGS...SaAAA
520-  553  (60.57/ 8.85)   AAAAA......AasgaGGAG..GGYGWGDGGYSSDSaaA.AAA
564-  586  (54.00/ 6.36)   ...........A....GGAG..GGYGWGDDGYGSDS...A.AAA
598-  620  (56.77/ 7.41)   ...........A....GGRG..GGYGWGDGGYGSDS...A.AAA
621-  648  (61.78/ 9.30)   AAAAA.....aA....AGSG..AG.GRGDGGYGSGS...S.AAA
675-  705  (67.06/11.30)   AAAAA...asgA....GGSG..GSYGWGDGGYGSDS...A.AAA
712-  740  (59.87/ 8.58)   AAASG......A....GGSGgyGGYG.GYGGYGSDS...A.AAA
755-  777  (55.19/ 6.81)   ...........A....GGVG..GGYGWGDGGYGSDS...A.AAA
778-  805  (61.78/ 9.30)   AAAAA.....aA....AGSG..AG.GRGDGGYGSGS...S.AAA
832-  863  (68.99/12.03)   AAAAA..aasgA....GCAG..GGYGWGDGGYGSDS...A.AAA
876-  898  (54.00/ 6.36)   ...........A....GGAG..GGYGWGDDGYGSDS...A.AAA
```

FIG. 5

```
Query_length: 14

Prediction:

GGYGXGDGGYGSDS

CCCCCCCCCCCCCC

.......T......

Where X = R or W.  (T=Turn;C=Random Coil)
```

FIG. 6

SEQUENCE LISTING

<160> NUMBER OF SEQ ID NOS: 187

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1

Pro Pro Ser Arg Asn
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 2

Lys Asn Glu Glu Asp
1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 3

Ser Ala Ala Arg Arg Ala Gly His Asp Arg Ala Ala Gly Ser
1               5                   10

<210> SEQ ID NO 4
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Ala Gly His Asp Arg Ala Ala Gly Ser
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Tyr Gly
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Gly Ser Asp
1

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Trp or Arg

<400> SEQUENCE: 7

Gly Gly Tyr Gly Xaa Gly Asp Gly Gly Tyr Gly Ser Asp Ser
1               5                   10

<210> SEQ ID NO 8
<211> LENGTH: 2000
<212> TYPE: PRT
<213> ORGANISM: Antheraea pernyi

<400> SEQUENCE: 8

Met Arg Val Ile Ala Phe Val Ile Leu Cys Cys Ala Leu Gln Tyr Ala
1               5                   10                  15

Thr Ala Lys Asn Leu Arg His His Asp Glu Tyr Val Asp Asn His Gly
                20                  25                  30

Gln Leu Val Glu Arg Phe Thr Thr Arg Lys His Phe Glu Arg Asn Ala
            35                  40                  45

Ala Thr Arg Pro His Leu Ser Gly Asn Glu Arg Leu Val Glu Thr Ile
        50                  55                  60

Val Leu Glu Glu Asp Pro Tyr Gly His Glu Asp Ile Tyr Glu Glu Asp
65                  70                  75                  80
```

-continued

Val Val Ile Lys Arg Val Pro Gly Ala Ser Ser Ala Ala Ala
            85              90              95

Ser Ser Ala Ser Ala Gly Ser Gly Gln Thr Ile Ile Val Glu Arg Gln
            100             105             110

Ala Ser His Gly Ala Gly Gly Ala Ala Gly Ala Ala Gly Ala Ala
            115             120             125

Ala Gly Ser Ser Ala Arg Arg Gly Gly Gly Phe Tyr Glu Thr His Asn
            130             135             140

Ser Tyr Ser Ser Tyr Gly Ser Gly Ser Ser Ser Ala Ala Ala Gly Ser
145             150             155             160

Gly Ala Gly Gly Val Gly Gly Gly Tyr Gly Ser Asp Ser Ala Ala Ala
            165             170             175

Ala Ala Ala Ala Ala Ala Ala Ala Ser Gly Ala Gly Gly Ser Gly Gly
            180             185             190

Tyr Gly Gly Tyr Gly Ser Asp Ser Ala Ala Ala Ala Ala Ala
            195             200             205

Ala Ala Ala Ala Ala Gly Ser Gly Ala Gly Gly Ser Gly Gly Tyr Gly
            210             215             220

Gly Tyr Gly Gly Tyr Gly Ser Asp Ser Ala Ala Ala Ala Ala Ala
225             230             235             240

Ala Ala Ala Ala Ala Ala Gly Ser Ser Ala Gly Gly Ala Gly Gly
            245             250             255

Tyr Gly Trp Gly Asp Gly Gly Tyr Gly Ser Asp Ser Ala Ala Ala
            260             265             270

Ala Ala Ala Ala Ala Ala Ala Ala Gly Ser Gly Ala Gly Gly Ser
            275             280             285

Gly Gly Tyr Gly Gly Tyr Gly Ser Asp Ser Ala Ala Ala Ala Ala
            290             295             300

Ala Ala Ala Ala Ala Ala Gly Ser Ser Ala Gly Gly Ala Gly Gly
305             310             315             320

Gly Tyr Gly Trp Gly Asp Gly Gly Tyr Gly Ser Asp Ser Ala Ala Ala
            325             330             335

Ala Ala Ala Ala Ala Ala Ala Ala Ser Ser Gly Ala Gly Gly Arg
            340             345             350

Gly Asp Gly Gly Tyr Gly Ser Gly Gly Ser Ser Ala Ala Ala Ala
            355             360             365

Ala Ala Ala Ala Ala Ala Arg Arg Ala Gly His Asp Arg Ala Ala
            370             375             380

Gly Ser Ala Ala Ala Ala Ala Ala Ala Ala Ala Ala Ala Ala Ser
385             390             395             400

Gly Ala Gly Gly Ser Gly Gly Tyr Gly Trp Gly Asp Gly Tyr
            405             410             415

Gly Ser Asp Ser Ala Ala Ala Ala Ala Ala Ala Ala Ala Ala
            420             425             430

Ala Gly Ser Gly Ala Gly Gly Ala Gly Gly Tyr Gly Trp Gly Asp
            435             440             445

Ser Gly Tyr Gly Ser Asp Ser Ala Ala Ala Ala Ala Ala Ala Ala
            450             455             460

Ala Ala Ala Ser Gly Ala Gly Gly Ser Gly Gly Tyr Gly Gly Tyr
465             470             475             480

Gly Ser Asp Ser Ala Ala Ala Ala Ala Ala Ala Ala Ala Ala
            485             490             495

```
Ala Gly Ala Gly Ala Gly Ala Gly Ser Tyr Gly Trp Gly Asp
            500             505             510
Gly Gly Tyr Gly Ser Asp Ser Ala Ala Ala Ala Ala Ala Ala
        515             520             525
Ala Ala Ala Gly Ser Gly Ala Gly Gly Arg Gly Asp Gly Gly Tyr Gly
    530             535             540
Ser Gly Ser Ser Ala Ala Ala Ala Ala Ala Ala Ala Ala Ser Ala
545             550             555             560
Ala Arg Arg Ala Gly His Asp Ser Ala Ala Gly Ser Ala Ala Ala
            565             570             575
Ala Ala Ala Ala Ala Ala Ala Ala Ser Gly Ala Gly Gly Ser Gly
        580             585             590
Gly Gly Tyr Gly Trp Gly Asp Gly Gly Tyr Gly Ser Asp Ser Ala Ala
        595             600             605
Ala Ala Ala Ala Ala Ala Ala Ala Ala Gly Ser Gly Ala Gly
    610             615             620
Gly Ala Gly Gly Tyr Gly Trp Gly Asp Gly Gly Tyr Gly Ser Asp
625             630             635             640
Ser Ala Ala Ala Ala Ala Ala Ala Ala Ala Ala Ala Ser Gly
            645             650             655
Ala Arg Gly Ser Gly Gly Tyr Gly Gly Tyr Gly Ser Asp Ser Ala Ala
        660             665             670
Ala Ala Ala Ala Ala Ala Ala Ala Ala Gly Ser Gly Ala Gly
    675             680             685
Gly Val Gly Gly Tyr Gly Trp Gly Asp Gly Gly Tyr Gly Ser Asp
690             695             700
Ser Ala Ala Ala Ala Ala Ala Ala Ala Ala Ala Gly Ser Gly
705             710             715             720
Ala Gly Gly Arg Gly Asp Gly Gly Tyr Gly Ser Gly Ser Ala Ala
            725             730             735
Ala Ala Ala Ala Ala Ala Ala Ser Ala Ala Arg Arg Ala Gly His
        740             745             750
Asp Ser Ala Ala Gly Ser Ala Ala Ala Ala Ala Ala Ala Ala
            755             760             765
Ala Ala Ala Ser Gly Ala Gly Gly Ser Gly Gly Gly Tyr Gly Trp Gly
    770             775             780
Asp Gly Gly Tyr Gly Ser Asp Ser Ala Ala Ala Ala Ala Ala Ala
785             790             795             800
Ala Ala Ala Ala Ala Gly Ser Gly Ala Gly Gly Ala Gly Gly Tyr
            805             810             815
Gly Trp Gly Asp Gly Gly Tyr Gly Ser Asp Ser Ala Ala Ala Ala
        820             825             830
Ala Ala Ala Ala Ala Ala Ala Ser Gly Ala Arg Gly Ser Gly Gly
        835             840             845
Tyr Gly Gly Tyr Gly Ser Asp Ser Ala Ala Ala Ala Ala Ala Ala
    850             855             860
Ala Ala Ala Ala Ala Gly Ser Gly Ala Gly Gly Val Gly Gly Tyr
865             870             875             880
Gly Trp Gly Asp Gly Gly Tyr Gly Ser Asp Ser Ala Ala Ala Ala
            885             890             895
Ala Ala Ala Ala Ala Ala Ala Gly Ser Gly Ala Gly Arg Gly Asp
        900             905             910
Gly Gly Tyr Gly Ser Gly Ser Ser Ala Ala Ala Ala Ala Ala Ala Ala
```

-continued

```
            915                 920                 925
Ala Ala Ser Ala Ala Arg Arg Ala Gly His Asp Ser Ala Ala Gly Ser
            930                 935                 940
Ala Ala Ala Ala Ala Ala Ala Ala Ala Ala Ala Ser Gly Ala
945                 950                 955                 960
Gly Gly Ser Gly Gly Gly Tyr Gly Trp Gly Asp Gly Gly Tyr Gly Ser
                965                 970                 975
Asp Ser Ala Ala Ala Ala Ala Ala Ala Ala Ala Ala Ala Gly
            980                 985                 990
Ser Gly Ala Gly Gly Ala Gly Gly Gly Tyr Gly Trp Gly Asp Gly Gly
            995                 1000                1005
Tyr Gly Ser Asp Ser Ala Ala Ala Ala Ala Ala Ala Ala Ala
    1010                1015                1020
Ala Ala Ala Ser Gly Ala Arg Gly Ser Gly Gly Tyr Gly Gly Tyr
    1025                1030                1035
Gly Ser Asp Ser Ala Ala Ala Ala Ala Ala Ala Ala Ala Ala
    1040                1045                1050
Ala Ala Gly Ser Gly Ala Gly Gly Val Gly Gly Gly Tyr Gly Trp
    1055                1060                1065
Gly Asp Gly Gly Tyr Gly Ser Asp Ser Ala Ala Ala Ala Ala Ala
    1070                1075                1080
Ala Ala Ala Ala Ala Ala Gly Ser Gly Ala Gly Gly Arg Gly Asp
    1085                1090                1095
Gly Gly Tyr Gly Ser Gly Ser Ser Ala Ala Ala Ala Ala Ala
    1100                1105                1110
Ala Ala Ala Ala Ala Arg Arg Ala Gly His Asp Arg Ala Ala Gly
    1115                1120                1125
Ser Ala Ala Ala Ala Ala Ala Ala Ala Ala Ala Ala Ala Ser
    1130                1135                1140
Gly Ala Gly Gly Ser Gly Gly Gly Tyr Gly Trp Gly Asp Gly Gly
    1145                1150                1155
Tyr Gly Ser Asp Ser Ala Ala Ala Ala Ala Ala Ala Ala Ala
    1160                1165                1170
Ala Ala Ala Ala Ser Gly Ala Gly Gly Ser Gly Gly Tyr Gly Gly
    1175                1180                1185
Tyr Gly Ser Asp Ser Ala Ala Ala Ala Ala Ala Ala Ala Ala
    1190                1195                1200
Ala Ala Ala Gly Ser Gly Ala Gly Gly Ala Gly Gly Tyr Gly
    1205                1210                1215
Trp Gly Asp Gly Gly Tyr Gly Ser Asp Ser Ala Ala Ala Ala Ala
    1220                1225                1230
Ala Ala Ala Ala Ala Ala Ala Ser Gly Ala Gly Gly Ser Gly
    1235                1240                1245
Gly Tyr Gly Gly Tyr Gly Gly Tyr Gly Ser Asp Ser Ala Ala Ala
    1250                1255                1260
Ala Ala Ala Ala Ala Ala Ala Ala Ala Gly Ser Gly Ala Gly
    1265                1270                1275
Gly Ala Gly Gly Gly Tyr Gly Trp Gly Asp Gly Gly Tyr Gly Ser
    1280                1285                1290
Asp Ser Ala Ala Ala Ala Ala Ala Ala Ala Ala Ala Ala Gly
    1295                1300                1305
Ser Gly Ala Gly Gly Arg Gly Asp Gly Gly Tyr Gly Ser Gly Ser
    1310                1315                1320
```

-continued

Ser Ala Ala Ala Ala Ala Ala Ala Ala Ala Ala Ala Arg
1325                1330                1335

Arg Ala Gly His Asp Arg Ala Ala Gly Ser Ala Ala Ala
1340                1345                1350

Ala Ala Ala Ala Ala Ala Ala Ser Gly Ala Gly Gly Ser Gly
1355                1360                1365

Gly Gly Tyr Gly Trp Gly Asp Gly Gly Tyr Gly Ser Asp Ser Ala
1370                1375                1380

Ala Ala Ala Ala Ala Ala Ala Ala Ala Ala Ala Ala Ser Gly
1385                1390                1395

Ala Gly Gly Ser Gly Gly Tyr Gly Gly Tyr Gly Ser Asp Ser Ala
1400                1405                1410

Ala Ala Ala Ala Ala Ala Ala Ala Ala Ala Ala Gly Ser Gly
1415                1420                1425

Ala Gly Gly Val Gly Gly Gly Tyr Gly Trp Gly Asp Gly Gly Tyr
1430                1435                1440

Gly Ser Asp Ser Ala Ala Ala Ala Ala Ala Ala Ala Ala Ala
1445                1450                1455

Ala Ala Ser Gly Ala Gly Gly Ser Gly Gly Tyr Gly Gly Tyr Gly
1460                1465                1470

Ser Asp Ser Ala Ala Ala Ala Ala Ala Ala Ala Ala Ala Ala
1475                1480                1485

Ala Ala Ser Gly Ala Gly Gly Ala Gly Gly Tyr Gly Gly Tyr Gly
1490                1495                1500

Ser Asp Ser Ala Ala Ala Ala Ala Ala Ala Ala Ala Ala Ala
1505                1510                1515

Ala Gly Ser Gly Ala Gly Gly Ala Gly Gly Gly Tyr Gly Trp Gly
1520                1525                1530

Asp Gly Gly Tyr Gly Ser Tyr Ser Ala Ala Ala Ala Ala Ala
1535                1540                1545

Ala Ala Ala Ala Ala Gly Ser Gly Ala Gly Gly Arg Gly Asp Gly
1550                1555                1560

Gly Tyr Gly Ser Gly Ser Ser Ala Ala Ala Ala Ala Ala Ala
1565                1570                1575

Ala Ala Ala Ala Arg Arg Ala Gly His Asp Arg Ala Ala Gly Ser
1580                1585                1590

Ala Ala Ala Ala Ala Ala Ala Ala Ala Ala Ala Ala Ser Gly
1595                1600                1605

Ala Gly Gly Ala Gly Gly Gly Tyr Gly Trp Gly Asp Gly Gly Tyr
1610                1615                1620

Ser Ser Asp Ser Ala Ala Ala Ala Ala Ala Ala Ala Ala Ala
1625                1630                1635

Ala Ala Gly Ser Gly Ala Gly Gly Ala Gly Gly Gly Tyr Gly Trp
1640                1645                1650

Gly Asp Asp Gly Tyr Gly Ser Asp Ser Ala Ala Ala Ala Ala
1655                1660                1665

Ala Ala Ala Ala Ala Ala Gly Ser Gly Ala Gly Gly Arg Gly Gly
1670                1675                1680

Gly Tyr Gly Trp Gly Asp Gly Gly Tyr Gly Ser Asp Ser Ala Ala
1685                1690                1695

Ala Ala Ala Ala Ala Ala Ala Ala Ala Gly Ser Gly Ala Gly
1700                1705                1710

-continued

Gly Arg Gly Asp Gly Gly Tyr Gly Ser Gly Ser Ser Ala Ala Ala
    1715                1720                1725

Ala Ala Ala Ala Ala Ala Ala Ala Ala Arg Arg Ala Gly His Asp
    1730                1735                1740

Arg Ala Ala Gly Ser Ala Ala Ala Ala Ala Ala Ala Ala Ala Ala
    1745                1750                1755

Ala Ala Ser Gly Ala Gly Gly Ser Gly Gly Ser Tyr Gly Trp Gly
    1760                1765                1770

Asp Gly Gly Tyr Gly Ser Asp Ser Ala Ala Ala Ala Ala Ala Ala
    1775                1780                1785

Ala Ala Ala Ala Ala Ala Ser Gly Ala Gly Gly Ser Gly Gly Tyr
    1790                1795                1800

Gly Gly Tyr Gly Gly Tyr Gly Gly Tyr Gly Ser Asp Ser Ala Ala
    1805                1810                1815

Ala Ala Ala Ala Ala Ala Ala Ala Ala Ala Ala Ala Ala Gly Ser
    1820                1825                1830

Gly Ala Gly Gly Val Gly Gly Gly Tyr Gly Trp Gly Asp Gly Gly
    1835                1840                1845

Tyr Gly Ser Asp Ser Ala Ala Ala Ala Ala Ala Ala Ala Ala Ala
    1850                1855                1860

Ala Ala Gly Ser Gly Ala Gly Gly Arg Gly Asp Gly Gly Tyr Gly
    1865                1870                1875

Ser Gly Ser Ser Ala Ala Ala Ala Ala Ala Ala Ala Ala Ala Ala
    1880                1885                1890

Ala Arg Arg Ala Gly His Asp Arg Ala Ala Gly Ser Ala Ala Ala
    1895                1900                1905

Ala Ala Ala Ala Ala Ala Ala Ala Ala Ser Gly Ala Gly Gly
    1910                1915                1920

Ala Gly Gly Gly Tyr Gly Trp Gly Asp Gly Gly Tyr Gly Ser Asp
    1925                1930                1935

Ser Ala Ala Ala Ala Ala Ala Ala Ala Ala Ala Ala Ala Ala Gly
    1940                1945                1950

Ser Gly Ala Gly Gly Ala Gly Gly Gly Tyr Gly Trp Gly Asp Asp
    1955                1960                1965

Gly Tyr Gly Ser Asp Ser Ala Ala Ala Ala Ala Ala Ala Ala Ala
    1970                1975                1980

Ala Ala Ala Gly Ser Gly Ala Gly Gly Arg Gly Gly Gly Tyr Gly
    1985                1990                1995

Trp Gly
    2000

<210> SEQ ID NO 9
<211> LENGTH: 2655
<212> TYPE: PRT
<213> ORGANISM: Antheraea yamamai

<400> SEQUENCE: 9

Met Arg Val Thr Ala Phe Val Ile Leu Cys Cys Ala Leu Gln Tyr Ala
1               5                   10                  15

Thr Ala Asn Asn Leu His His His Asp Glu Tyr Val Asp Asn His Gly
            20                  25                  30

Gln Leu Val Glu Arg Phe Thr Thr Arg Lys His Tyr Glu Arg Asn Ala
        35                  40                  45

Ala Thr Arg Pro His Leu Ser Gly Asn Glu Arg Leu Val Glu Thr Ile
    50                  55                  60

```
Val Leu Glu Glu Asp Pro Tyr Gly His Glu Asp Ile Tyr Glu Glu Asp
 65                  70                  75                  80
Val Val Ile Asn Arg Val Pro Gly Ala Ser Ser Ala Ala Ala Ala Ala
                 85                  90                  95
Ser Ser Ala Ser Ala Gly Ser Gly Gln Thr Ile Ile Val Glu Arg Gln
            100                 105                 110
Ala Ser His Gly Ala Gly Gly Ala Ala Gly Ala Ala Ala Gly Ala Ala
            115                 120                 125
Ala Gly Ser Ser Ala Arg Gly Gly Ser Gly Phe Tyr Glu Thr His Asp
        130                 135                 140
Ser Tyr Ser Ser Tyr Gly Ser Gly Ser Ser Ala Ala Ala Ala Ala Ser
145                 150                 155                 160
Ser Gly Ala Gly Gly Ala Gly Gly Tyr Gly Trp Gly Asp Gly Gly
                165                 170                 175
Tyr Gly Ser Asp Ser Ala Ala Ala Ala Ala Ala Ala Ala Ala Ala
                180                 185                 190
Ala Gly Ser Gly Ala Gly Gly Arg Gly Asp Gly Gly Tyr Gly Ser Gly
        195                 200                 205
Ser Ser Ala Ala Ala Ala Ala Ala Ala Ala Ala Ala Ala Ala Arg Arg
210                 215                 220
Ala Gly His Asp His Ala Ala Gly Ser Ser Gly Gly Tyr Ser Trp
225                 230                 235                 240
Asp Tyr Ser Ser Tyr Gly Ser Glu Ser Ala Ala Ala Ala Ala Ala
                245                 250                 255
Ala Ala Ala Gly Ser Gly Ala Gly Gly Val Gly Gly Tyr Gly Gly
            260                 265                 270
Gly Asp Gly Gly Tyr Gly Ser Gly Ser Ser Ala Ala Ala Ala Ala
        275                 280                 285
Ala Ala Ala Ala Ala Ala Arg Arg Ala Gly His Asp Arg Ala Ala Gly
        290                 295                 300
Ser Ala Ala Ala Ala Ala Ala Ala Ala Ala Ala Ala Ala Ala Ser Gly
305                 310                 315                 320
Ala Gly Gly Ser Gly Gly Tyr Gly Trp Gly Asp Gly Gly Tyr Gly
            325                 330                 335
Ser Asp Ser Ala Ala Ala Ala Ala Ala Ala Ala Ala Ala Ala Ala
            340                 345                 350
Gly Ser Gly Ala Gly Arg Ala Gly Gly Asp Tyr Gly Trp Gly Asp Gly
        355                 360                 365
Gly Tyr Gly Ser Asp Ser Ala Ala Ala Ala Ala Ala Ala Ala Ala
        370                 375                 380
Ala Ser Gly Ala Gly Gly Ser Gly Gly Gly Tyr Gly Trp Gly Asp Gly
385                 390                 395                 400
Gly Tyr Gly Ser Asp Ser Ala Ala Ala Ala Ala Ala Ala Ala Ala
                405                 410                 415
Ala Ser Gly Ala Gly Gly Ser Gly Gly Gly Tyr Gly Trp Gly Asp Gly
            420                 425                 430
Gly Tyr Gly Ser Asp Ser Ala Ala Ala Ala Ala Ala Ala Ala Ala
        435                 440                 445
Ala Ala Gly Ser Gly Gly Gly Arg Gly Asp Gly Gly Tyr Gly Ser
        450                 455                 460
Gly Ser Ser Ala Ala Ala Ala Ala Ala Ala Ala Ala Ala Ala Ala
465                 470                 475                 480
```

```
Arg Gln Ala Gly His Glu Arg Ala Ala Gly Ser Ala Ala Ala Ala
                    485                 490                 495
Ala Ala Ala Ala Ala Ala Ala Ala Ser Gly Ala Gly Ser Gly Arg
                500                 505                 510
Gly Tyr Gly Trp Gly Asp Gly Tyr Gly Ser Asp Ser Ala Ala Ala
                515                 520                 525
Ala Ala Ala Ala Ala Ala Ala Ala Gly Ser Gly Ala Gly Gly
        530                 535                 540
Ala Gly Gly Asp Tyr Gly Trp Gly Asp Gly Tyr Gly Ser Asp Ser
545                 550                 555                 560
Ala Ala Ala Ala Ala Ala Ala Ala Ala Ser Gly Ala Gly Gly
                565                 570                 575
Ser Gly Gly Gly Tyr Gly Trp Gly Asp Gly Tyr Gly Ser Asp Ser
                580                 585                 590
Ala Ala Ala Ala Ala Ala Ala Ala Ala Ala Gly Ser Gly Ala
                595                 600                 605
Gly Gly Arg Gly Asp Gly Tyr Gly Ser Gly Ser Ala Ala Ala
        610                 615                 620
Ala Ala Ala Ala Ala Ala Ala Ala Arg Arg Ala Gly His Asp Arg
625                 630                 635                 640
Ala Ala Gly Ser Ala Ala Ala Ala Ala Ala Ala Ala Ala Ala
                645                 650                 655
Ser Gly Ala Gly Gly Ser Gly Gly Tyr Gly Trp Gly Asp Gly Gly
                660                 665                 670
Tyr Gly Ser Asp Ser Ala Ala Ala Ala Ala Ala Ala Ala Ala
        675                 680                 685
Ala Ala Gly Ser Gly Ala Gly Gly Ala Gly Gly Asp Tyr Gly Trp Gly
        690                 695                 700
Asp Gly Gly Tyr Gly Ser Asp Ser Ala Ala Ala Ala Ala Ala Ala
705                 710                 715                 720
Ala Ala Ala Ser Gly Ala Gly Gly Ala Gly Gly Tyr Gly Trp Gly
                725                 730                 735
Asp Gly Gly Tyr Gly Ser Asp Ser Ala Ala Ala Ala Ala Ala Ala
                740                 745                 750
Ala Ala Ala Ala Gly Ser Gly Ala Gly Gly Arg Gly Asp Gly Gly Tyr
                755                 760                 765
Gly Ser Gly Ser Ser Ala Ala Ala Ala Ala Ala Ala Ala Ala
        770                 775                 780
Ala Arg Arg Ala Gly His Asp Arg Ala Ala Gly Ser Ala Ala Ala
785                 790                 795                 800
Ala Ala Ala Ala Ala Ala Ala Ala Ser Gly Ala Gly Gly Ser Gly
                805                 810                 815
Gly Gly Tyr Gly Trp Gly Asp Gly Gly Tyr Gly Ser Asp Ser Ala Ala
                820                 825                 830
Ala Ala Ala Ala Ala Ala Ala Ala Ala Ala Gly Ser Gly Ala Gly
        835                 840                 845
Gly Ala Gly Gly Asp Tyr Gly Trp Gly Asp Gly Gly Tyr Gly Ser Asp
        850                 855                 860
Ser Ala Ala Ala Ala Ala Ala Ala Ala Ala Ala Ser Gly Ala Gly
865                 870                 875                 880
Gly Ser Gly Gly Gly Tyr Gly Trp Gly Asp Gly Gly Tyr Gly Ser Asp
                885                 890                 895
Ser Ala Ala Ala Ala Ala Ala Ala Ala Ala Ala Ala Ala Gly Ser Gly
```

-continued

```
                900             905             910
Ala Gly Gly Arg Gly Asp Gly Tyr Gly Ser Gly Ser Ala Ala
            915             920             925
Ala Ala Ala Ala Ala Ala Ala Ala Arg Arg Ala Gly His Asp
            930             935             940
Arg Ala Ala Gly Ser Ala Ala Ala Ala Ala Ala Ala Ala Ala
945             950             955             960
Ala Ala Ser Gly Ala Gly Gly Ser Gly Gly Tyr Gly Trp Gly Asp
            965             970             975
Gly Gly Tyr Gly Ser Asp Ser Ala Ala Ala Ala Ala Ala Ala
            980             985             990
Ala Ala Ala Ala Gly Ser Gly Ala Gly Gly Ala Gly Gly Asp Tyr Gly
            995             1000            1005
Trp Gly Asp Gly Gly Tyr Gly Ser Asp Ser Ala Ala Ala Ala
    1010            1015            1020
Ala Ala Ala Ala Ala Ala Ser Gly Ala Gly Gly Ala Gly Gly Gly
    1025            1030            1035
Tyr Gly Trp Gly Asp Gly Gly Tyr Gly Ser Asp Ser Ala Ala Ala
    1040            1045            1050
Ala Ala Ala Ala Ala Ala Ala Ala Gly Ser Gly Ala Gly Gly
    1055            1060            1065
Arg Gly Asp Gly Gly Tyr Gly Ser Gly Ser Ser Ala Ala Ala Ala
    1070            1075            1080
Ala Ala Ala Ala Ala Ala Ala Arg Arg Ala Gly His Asp Arg
    1085            1090            1095
Ala Ala Gly Ser Ala Ala Ala Ala Ala Ala Ala Ala Ala Ala
    1100            1105            1110
Ala Ala Ser Gly Ala Gly Gly Ser Gly Gly Gly Tyr Gly Trp Gly
    1115            1120            1125
Asp Gly Gly Tyr Gly Ser Asp Ser Ala Ala Ala Ala Ala Ala Ala
    1130            1135            1140
Ala Ala Ala Ala Ala Ala Gly Ser Gly Ala Gly Gly Val Gly Gly
    1145            1150            1155
Gly Tyr Gly Trp Gly Asp Gly Gly Tyr Gly Ser Asp Ser Ala Ala
    1160            1165            1170
Ala Ala Ala Ala Ala Ala Ala Ala Ala Ala Ser Gly Ala Gly
    1175            1180            1185
Gly Ala Gly Gly Tyr Gly Tyr Gly Ser Asp Ser Ala Ala Ala
    1190            1195            1200
Ala Ala Ala Ala Ala Ala Ala Ala Ala Ser Ser Gly Ala Gly
    1205            1210            1215
Gly Ala Gly Gly Gly Tyr Gly Trp Gly Asp Gly Gly Tyr Gly Ser
    1220            1225            1230
Asp Ser Ala Ala Ala Ala Ala Ala Ala Ala Ala Ala Ala Gly
    1235            1240            1245
Ser Gly Ala Gly Gly Arg Gly Asp Gly Gly Tyr Gly Ser Gly Ser
    1250            1255            1260
Ser Ala Ala Ala Ala Ala Ala Ala Ala Ala Ala Ala Ala Ser
    1265            1270            1275
Gly Ala Gly Gly Ser Gly Gly Gly Tyr Gly Trp Gly Asp Gly Gly
    1280            1285            1290
Tyr Gly Ser Gly Ser Ala Ala Ala Ala Ala Ala Ala Ala Ala Ala
    1295            1300            1305
```

```
Ala Ala  Ala Gly Ser Gly Ala  Gly Gly Val Gly Gly  Gly Tyr Gly
    1310             1315                 1320

Trp Gly  Asp Gly Gly Tyr Gly  Ser Asp Ser Ala Ala  Ala Ala Ala
    1325             1330                 1335

Ala Ala  Ala Ala Ala Ala Ala  Ala Ser Gly Ala Gly  Gly Ala Gly
    1340             1345                 1350

Gly Tyr  Gly Gly Tyr Gly Ser  Asp Ser Ala Ala Ala  Ala Ala Ala
    1355             1360                 1365

Ala Ala  Ala Ala Ala Ala Ala  Gly Ser Gly Ala Gly  Gly Ala Gly
    1370             1375                 1380

Gly Gly  Tyr Gly Trp Gly Asp  Gly Gly Tyr Gly Ser  Asp Ser Ala
    1385             1390                 1395

Ala Ala  Ala Ala Ala Ala Ala  Ala Ala Ala Ala Ala  Ser Gly Ala
    1400             1405                 1410

Gly Gly  Arg Gly Asp Gly Gly  Tyr Gly Ser Gly Ser  Ser Ala Ala
    1415             1420                 1425

Ala Ala  Ala Ala Ala Ala Ala  Ala Ala Ala Arg Arg  Ala Gly Tyr
    1430             1435                 1440

Asp Arg  Ala Ala Gly Ser Ala  Ala Ala Ala Ala Ala  Ala Ala Ala
    1445             1450                 1455

Ala Ala  Ala Ala Ser Gly Ala  Gly Gly Ser Gly Gly  Gly Tyr Gly
    1460             1465                 1470

Trp Gly  Asp Gly Gly Tyr Gly  Ser Asp Ser Ala Ala  Ala Ala Ala
    1475             1480                 1485

Ala Ala  Ala Ala Ala Ala Ala  Ala Ser Gly Ala Gly  Gly Ala Gly
    1490             1495                 1500

Gly Tyr  Gly Gly Tyr Gly Ser  Asp Ser Ala Ala Ala  Ala Ala Ala
    1505             1510                 1515

Ala Ala  Ala Ala Ala Ala Ala  Gly Ser Gly Ala Gly  Gly Ala Gly
    1520             1525                 1530

Gly Gly  Tyr Gly Trp Gly Asp  Gly Gly Tyr Gly Ser  Asp Ser Ala
    1535             1540                 1545

Ala Ala  Ala Ala Ala Ala Ala  Ala Ala Ala Ala Ala  Ser Gly Ala
    1550             1555                 1560

Gly Gly  Arg Gly Asp Gly Gly  Tyr Gly Ser Gly Ser  Ser Ala Ala
    1565             1570                 1575

Ala Ala  Ala Ala Ala Ala Ala  Ala Ala Ala Arg Arg  Ala Gly Tyr
    1580             1585                 1590

Asp Arg  Ala Ala Gly Ser Ala  Ala Ala Ala Ala Ala  Ala Ala Ala
    1595             1600                 1605

Ala Ala  Ala Ala Ser Gly Ala  Gly Gly Ser Gly Gly  Gly Tyr Gly
    1610             1615                 1620

Trp Gly  Asp Gly Gly Tyr Gly  Ser Asp Ser Ala Ala  Ala Ala Ala
    1625             1630                 1635

Ala Ala  Ala Ala Ala Ala Ala  Ala Ser Gly Ala Gly  Gly Ala Gly
    1640             1645                 1650

Gly Tyr  Gly Gly Tyr Gly Ser  Asp Ser Ala Ala Ala  Ala Ala Ala
    1655             1660                 1665

Ala Ala  Ala Ala Ala Ala Ala  Gly Ser Gly Ala Gly  Gly Ala Gly
    1670             1675                 1680

Gly Gly  Tyr Gly Trp Gly Asp  Gly Gly Tyr Gly Ser  Asp Ser Ala
    1685             1690                 1695
```

-continued

Ala Ala Ala Ala Ala Ala Ala Ala Ala Ala Gly Ser Gly Ala
1700                1705                1710

Gly Gly Arg Gly Asp Gly Gly Tyr Gly Ser Gly Ser Ser Ala Ala
1715                1720                1725

Ala Ala Ala Ala Ala Ala Ala Ala Ala Ala Arg Arg Ala Gly
1730                1735                1740

His Asp Arg Ala Ala Gly Cys Ala Ala Ala Ala Ala Ala Ala
1745                1750                1755

Ala Ala Ala Ala Ser Gly Ala Gly Gly Ser Gly Gly Gly Tyr Gly
1760                1765                1770

Trp Gly Asp Gly Gly Tyr Gly Ser Asp Ser Ala Ala Ala Ala
1775                1780                1785

Ala Ala Ala Ala Ala Ala Ala Ala Gly Ser Gly Ala Gly Gly Ala
1790                1795                1800

Gly Gly Gly Tyr Gly Trp Gly Asp Gly Gly Tyr Gly Ser Asp Ser
1805                1810                1815

Ala Ala Ala Ala Ala Ala Ala Ala Ala Ala Ser Gly Ala Gly
1820                1825                1830

Gly Thr Gly Gly Gly Tyr Gly Trp Gly Asp Gly Gly Tyr Gly Ser
1835                1840                1845

Asp Ser Ala Ala Ala Ala Ala Ala Ala Ala Ala Ala Ala Ser Gly
1850                1855                1860

Ala Gly Gly Ala Gly Gly Gly Tyr Gly Trp Gly Asp Gly Gly Tyr
1865                1870                1875

Gly Ser Asp Ser Ala Ala Ala Ala Ala Ala Ala Ala Ala Ala
1880                1885                1890

Ala Gly Ser Gly Ala Gly Gly Arg Gly Asp Gly Gly Tyr Gly Ser
1895                1900                1905

Gly Ser Ser Ala Ala Ala Ala Ala Ala Ala Ala Ala Ala Ala
1910                1915                1920

Arg Arg Ala Gly His Asp Arg Ala Ala Gly Ser Ala Ala Ala Ala
1925                1930                1935

Ala Ala Ala Ala Ala Ala Ala Ala Ala Ser Gly Ala Gly Gly Ser
1940                1945                1950

Gly Gly Gly Tyr Gly Trp Gly Asp Gly Gly Tyr Gly Ser Asn Ser
1955                1960                1965

Ala Ala Ala Ala Ala Ala Ala Ala Ala Ala Ala Ala Gly Ser
1970                1975                1980

Gly Ala Gly Gly Val Gly Gly Gly Tyr Gly Trp Gly Asp Gly Gly
1985                1990                1995

Tyr Gly Ser Asp Ser Ala Ala Ala Ala Ala Ala Ala Ala Ala
2000                2005                2010

Ala Ala Ala Gly Ser Gly Ala Gly Gly Ala Gly Gly Gly Tyr Gly
2015                2020                2025

Trp Gly Asp Gly Gly Tyr Gly Ser Asp Ser Ala Ala Ala Ala Ala
2030                2035                2040

Ala Ala Ala Ala Ala Ala Ala Gly Ser Gly Ala Gly Gly Arg Gly
2045                2050                2055

Asp Gly Gly Tyr Gly Ser Gly Ser Ser Ala Ala Ala Ala Ala Ala
2060                2065                2070

Ala Ala Ala Ala Ala Ala Arg Arg Ala Gly His Asp Arg Ala Ala
2075                2080                2085

Gly Ser Ala Ala Ala Ala Ala Ala Ala Ala Ala Ala Ala Ala Ala

-continued

```
            2090                2095                2100
Ser Gly Ala Gly Arg Ser Gly Gly Tyr Gly Trp Gly Asp Gly
    2105                2110                2115
Gly Tyr Ser Ser Asp Ser Ala Ala Ala Ala Ala Ala Ala Ala
    2120                2125                2130
Ala Ala Ala Ala Gly Ser Gly Ala Gly Gly Val Gly Gly Tyr
    2135                2140                2145
Gly Trp Gly Asp Gly Gly Tyr Gly Ser Asp Ser Ala Ala Ala
    2150                2155                2160
Ala Ala Ala Ala Ala Ala Ala Ser Gly Ala Gly Gly Ser Gly Gly
    2165                2170                2175
Tyr Gly Gly Tyr Gly Ser Asp Ser Ala Ala Ala Ala Ala Ala
    2180                2185                2190
Ala Ala Ala Ala Ala Ala Gly Ser Gly Ala Gly Gly Val Gly Gly
    2195                2200                2205
Gly Tyr Gly Trp Gly Asp Gly Tyr Gly Ser Asp Ser Ala Ala
    2210                2215                2220
Ala Ala Ala Ala Ala Ala Ala Ser Gly Ala Gly Gly Ser
    2225                2230                2235
Gly Gly Tyr Gly Gly Tyr Gly Ser Asp Ser Ala Ala Ala Ala
    2240                2245                2250
Ala Ala Ala Ala Ala Ala Ala Gly Ser Gly Ala Gly Gly Val
    2255                2260                2265
Gly Gly Gly Tyr Gly Trp Asp Gly Gly Tyr Gly Gly Tyr Gly
    2270                2275                2280
Ser Asp Ser Ala Ala Ala Ala Ala Ala Ala Ala Ala Ala Gly
    2285                2290                2295
Ser Gly Ala Gly Gly Val Gly Gly Tyr Gly Arg Gly Asp Ser
    2300                2305                2310
Gly Tyr Gly Ser Gly Ser Ser Ala Ala Ala Ala Ala Ala Ala
    2315                2320                2325
Ala Ala Ala Arg Arg Ala Gly His Gly Arg Ser Ser Gly Ser Ala
    2330                2335                2340
Ala Ala Ala Ala Ala Ala Ala Ala Ala Ala Ala Ser Gly Ala
    2345                2350                2355
Gly Gly Ser Gly Gly Gly Tyr Gly Trp Asp Tyr Gly Ser Tyr Gly
    2360                2365                2370
Ser Asp Ser Ala Ala Ala Ala Ala Ala Ala Ala Ala Ala Ala
    2375                2380                2385
Ser Ser Gly Ala Gly Gly Ser Gly Gly Gly Tyr Gly Trp Asp Tyr
    2390                2395                2400
Gly Gly Tyr Gly Ser Asp Ser Ala Ala Ala Ala Ala Ala Ala
    2405                2410                2415
Ala Ala Ala Ala Gly Ser Gly Ala Gly Gly Ser Gly Gly Tyr
    2420                2425                2430
Gly Trp Gly Asp Gly Gly Tyr Gly Ser Asp Ser Ala Ala Ala
    2435                2440                2445
Ala Ala Ala Ala Ala Ala Ala Gly Ser Gly Ala Gly Gly Arg
    2450                2455                2460
Gly Asp Gly Gly Tyr Gly Ser Gly Ser Ser Ala Ala Ala Ala
    2465                2470                2475
Ala Ala Ala Ala Ala Ala Ala Arg Arg Ala Gly His Asp His Ala
    2480                2485                2490
```

```
Ala Gly Ser Ser Gly Gly Gly Tyr Ser Trp Asp Tyr Ser Ser Tyr
    2495                2500                2505

Gly Ser Glu Ser Ala Ala Ala Ala Ala Ala Ala Ala Ala Ala Gly
    2510                2515                2520

Ser Gly Ala Gly Gly Val Gly Gly Gly Tyr Gly Gly Gly Asp Gly
    2525                2530                2535

Gly Tyr Gly Ser Gly Ser Ser Ala Ala Ala Ala Ala Ala Ala Ala
    2540                2545                2550

Ala Ala Ala Ala Ser Arg Arg Ala Gly His Asp Arg Ala Tyr Gly
    2555                2560                2565

Ala Gly Ser Ala Ala Ala Ala Ala Ala Ala Ala Ala Ala Gly Ala
    2570                2575                2580

Gly Ala Ser Arg Pro Val Gly Ile Tyr Gly Thr Asp Asp Gly Phe
    2585                2590                2595

Val Leu Asp Gly Gly Tyr Asp Ser Glu Gly Ser Ala Ala Ala Ala
    2600                2605                2610

Ala Ala Ala Ala Ala Ala Ala Ala Ser Ser Ser Gly Arg Ser Thr
    2615                2620                2625

Glu Gly His Pro Leu Leu Ser Ile Cys Cys Arg Pro Cys Ser His
    2630                2635                2640

Arg His Ser Tyr Glu Ala Ser Arg Ile Ser Val His
    2645                2650                2655

<210> SEQ ID NO 10
<211> LENGTH: 507
<212> TYPE: PRT
<213> ORGANISM: Antheraea militta

<400> SEQUENCE: 10

Met Arg Val Ile Ala Phe Val Ile Leu Cys Cys Ala Leu Gln Tyr Ala
1               5                   10                  15

Thr Ala Lys Asn Ile His His Asp Glu Tyr Val Asp Ser His Gly Gln
            20                  25                  30

Leu Val Glu Arg Phe Thr Thr Arg Lys His Tyr Glu Arg Asn Ala Ala
        35                  40                  45

Thr Arg Pro His Leu Ser Gly Asn Glu Arg Leu Val Glu Thr Ile Val
    50                  55                  60

Leu Glu Glu Asp Pro Tyr Gly His Glu Asp Ile Tyr Glu Glu Asp Val
65                  70                  75                  80

Val Ile Lys Arg Val Pro Gly Ala Ser Ser Ala Ala Ala Ala Ser
                85                  90                  95

Ser Ala Ser Ala Gly Ser Gly Gln Thr Ile Thr Val Glu Arg Gln Ala
            100                 105                 110

Ser His Gly Ala Gly Gly Ala Ala Gly Ala Ala Gly Ala Ala Ala
        115                 120                 125

Ser Ser Ser Val Arg Gly Gly Gly Phe Tyr Glu Thr His Asp Ser
    130                 135                 140

Tyr Ser Ser Tyr Gly Ser Asp Ser Ala Ala Ala Ala Ala Ala Ala
145                 150                 155                 160

Ala Ser Gly Ala Gly Gly Arg Gly His Gly Gly Tyr Gly Ser Asp Ser
                165                 170                 175

Ala Ala Ala Ala Ala Ala Ala Ala Ala Ala Ala Ala Ala Ser
            180                 185                 190

Gly Ala Gly Gly Arg Gly His Gly Gly Tyr Gly Ser Asp Ser Ala Ala
```

-continued

```
                195                 200                 205
Ala Ala Ala Ala Ala Ala Ala Ala Ala Gly Ser Gly Ala
        210                 215                 220

Gly Gly Arg Gly Asp Gly Gly Tyr Gly Trp Gly Asp Gly Gly Tyr Gly
225                 230                 235                 240

Ser Asp Ser Gly Ala Ala Ala Ala Ala Ala Ala Ala Ala Ala Ala
                245                 250                 255

Ala Ser Gly Ala Gly Gly Arg Gly Asp Gly Gly Tyr Gly Arg Gly Asp
            260                 265                 270

Gly Gly Tyr Gly Ser Asp Ser Ala Ala Ala Ala Ala Ala Ala
                275                 280                 285

Ala Ala Ala Gly Ser Gly Ala Gly Gly Gln Ala Thr Val Val Met Asp
            290                 295                 300

Gly Ala Met Ala Ala Met Val Leu Thr Arg Ala Gln Gln Gln Leu Ala
305                 310                 315                 320

Ala Ala Ala Ala Ala Ser Ala Ser Gly Ala Gly Gly Ser Gly Gly
                325                 330                 335

Ser Tyr Glu Trp Asp Tyr Gly Ser Tyr Gly Ser Asp Ser Ala Ala Ala
            340                 345                 350

Ala Ala Ala Ala Ala Ala Ala Ala Gly Ser Gly Ala Gly Gly
                355                 360                 365

Val Gly Gly Gly Tyr Gly Arg Gly Asp Gly Gly Tyr Gly Ser Asp Ser
370                 375                 380

Ala Ala Ala Ala Ala Ala Ala Ala Ala Gly Ser Gly Ala
385                 390                 395                 400

Gly Gly Arg Gly Asp Gly Gly Tyr Gly Trp Gly Asp Gly Gly Tyr Gly
            405                 410                 415

Ser Asp Ser Gly Ala Ala Ala Ala Ala Ala Ala Ala Ala Ala
                420                 425                 430

Ala Ser Gly Ala Gly Gly Arg Gly Asp Gly Gly Tyr Gly Trp Gly Asp
            435                 440                 445

Gly Gly Tyr Gly Ser Asp Pro Gly Ala Ala Ala Ala Ala Ala
                450                 455                 460

Ala Ala Ala Ala Ala Ser Gly Ala Arg Gly Arg Gly Asp Gly Gly Tyr
465                 470                 475                 480

Gly Ser Gly Ser Ser Ala Ala Ala Ala Ala Ala Ala Ala Ala
                485                 490                 495

Ser Ala Ala Arg Arg Gly His Asp Arg Ala
                500                 505

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly Ala Ala Ala Gly Ala Ala Ala
1               5

<210> SEQ ID NO 12
<211> LENGTH: 29
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 12

Gly Ser Ser Ala Arg Arg Gly Gly Phe Tyr Glu Thr His Asn Ser
1               5                   10                  15

Tyr Ser Ser Tyr Gly Ser Gly Ser Ser Ala Ala Ala
            20                  25

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Ala Gly Gly Val Gly Gly Gly Tyr Gly Ser Asp Ser Ala
1               5                   10                  15

Ala Ala Ala Ala Ala Ala Ala Ala Ala
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ser Gly Ala Gly Gly Ser Gly Gly Tyr Gly Gly Tyr Gly Gly Tyr
1               5                   10                  15

Gly Ser Asp Ser Ala Ala Ala Ala Ala Ala Ala Ala Ala Ala Ala
            20                  25                  30

Ala

<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ser Ser Ala Gly Gly Ala Gly Gly Gly Tyr Gly Trp Asp Asp Gly
1               5                   10                  15

Gly Tyr Gly Ser Asp Ser Ala Ala Ala Ala Ala Ala Ala Ala Ala Ala

-continued

```
                 20                  25                  30

Ala Ala Ala
        35

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Gly Ala Gly Gly Ser Gly Gly Tyr Gly Gly Tyr Gly Ser Asp
1               5                   10                  15

Ser Ala Ala Ala Ala Ala Ala Ala Ala Ala Ala Ala Ala Ala
            20                  25                  30

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Ser Ala Gly Gly Ala Gly Gly Gly Tyr Gly Trp Asp Asp Gly
1               5                   10                  15

Gly Tyr Gly Ser Asp Ser Ala Ala Ala Ala Ala Ala Ala Ala Ala Ala
            20                  25                  30

Ala Ala

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ser Gly Ala Gly Gly Arg Gly Asp Gly Gly Tyr Gly Ser Gly Gly
1               5                   10                  15

Ser Ser Ala Ala Ala Ala Ala Ala Ala Ala Ala Ala Ala Ala
            20                  25                  30

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Ala Gly His Asp Arg Ala Ala Gly Ser Ala Ala Ala Ala Ala
1               5                   10                  15

Ala Ala Ala Ala Ala Ala Ala Ala
            20

<210> SEQ ID NO 21
<211> LENGTH: 34
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 21

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala Ala

<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Gly Ala Gly Gly Ala Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala
        35

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ala Gly Ala Gly Gly Ala Gly Gly Gly Tyr Gly Trp Gly Asp Gly
1               5                   10                  15

Gly Tyr Gly Ser Asp Ser Ala Ala Ala Ala Ala Ala Ala Ala Ala Ala
            20                  25                  30

Ala Ala

<210> SEQ ID NO 25
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Gly Ala Gly Gly Arg Gly Asp Gly Tyr Gly Ser Gly Ser
1               5                   10                  15

Ser Ala Ala Ala Ala Ala Ala Ala Ala Ala Ala
            20                  25

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ala Ala Arg Arg Ala Gly His Asp Ser Ala Ala Gly Ser Ala Ala
1               5                   10                  15

Ala Ala Ala Ala Ala Ala Ala Ala Ala Ala Ala
            20                  25

<210> SEQ ID NO 27
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala Ala

<210> SEQ ID NO 28
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ser Gly Ala Gly Gly Ala Gly Gly Gly Tyr Gly Trp Gly Asp Gly
1               5                   10                  15

Gly Tyr Gly Ser Asp Ser Ala Ala Ala Ala Ala Ala Ala Ala Ala Ala
            20                  25                  30

Ala Ala Ala
        35

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Ala Arg Gly Ser Gly Gly Tyr Gly Tyr Gly Ser Asp Ser
1               5                   10                  15

```
Ala Ala Ala Ala Ala Ala Ala Ala Ala Ala
            20                  25

<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ser Gly Ala Gly Gly Val Gly Gly Gly Tyr Gly Trp Gly Asp Gly
1               5                   10                  15

Gly Tyr Gly Ser Asp Ser Ala Ala Ala Ala Ala Ala Ala Ala Ala Ala
            20                  25                  30

Ala Ala

<210> SEQ ID NO 31
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala
            20                  25

<210> SEQ ID NO 32
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ala Ala Arg Arg Ala Gly His Asp Ser Ala Ala Gly Ser Ala Ala
1               5                   10                  15

Ala Ala Ala Ala Ala Ala Ala Ala Ala Ala Ala
            20                  25

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala Ala
            20                  25                  30

Ala Ala

<210> SEQ ID NO 34
<211> LENGTH: 35
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 34

Gly Ser Gly Ala Gly Gly Ala Gly Gly Tyr Gly Trp Gly Asp Gly
1               5                   10                  15

Gly Tyr Gly Ser Asp Ser Ala Ala Ala Ala Ala Ala Ala Ala Ala
                20                  25                  30

Ala Ala Ala
        35

<210> SEQ ID NO 35
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Gly Ala Arg Gly Ser Gly Gly Tyr Gly Gly Tyr Gly Ser Asp Ser
1               5                   10                  15

Ala Ala Ala Ala Ala Ala Ala Ala Ala Ala Ala Ala Ala
                20                  25

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Gly Ala Gly Gly Val Gly Gly Tyr Gly Trp Gly Asp Gly
1               5                   10                  15

Gly Tyr Gly Ser Asp Ser Ala Ala Ala Ala Ala Ala Ala Ala Ala
                20                  25                  30

Ala Ala

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala
                20                  25

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Ser Ala Ala Arg Arg Ala Gly His Asp Ser Ala Ala Gly Ser Ala Ala
1               5                   10                  15

Ala Ala Ala Ala Ala Ala Ala Ala Ala Ala
            20                  25
```

<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Ser Gly Ala Gly Gly Ser Gly Gly Tyr Gly Trp Gly Asp Gly Gly
1               5                   10                  15

Tyr Gly Ser Asp Ser Ala Ala Ala Ala Ala Ala Ala Ala Ala
            20                  25                  30

Ala Ala
```

<210> SEQ ID NO 40
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gly Ser Gly Ala Gly Gly Ala Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala
        35
```

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Ser Gly Ala Arg Gly Ser Gly Gly Tyr Gly Tyr Gly Ser Asp Ser
1               5                   10                  15

Ala Ala Ala Ala Ala Ala Ala Ala Ala Ala Ala Ala Ala Ala
            20                  25
```

<210> SEQ ID NO 42
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Gly Ser Gly Ala Gly Gly Val Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30
```

Ala Ala

<210> SEQ ID NO 43
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala
            20                  25

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Arg Ala Gly His Asp Arg Ala Ala Gly Ser Ala Ala Ala Ala Ala
1               5                   10                  15

Ala Ala Ala Ala Ala Ala Ala Ala
            20

<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala Ala
            20                  25                  30

Ala Ala

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 47
<211> LENGTH: 35
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 47

Gly Ser Gly Ala Gly Gly Ala Gly Gly Tyr Gly Trp Gly Asp Ser
1               5                   10                  15

Gly Tyr Gly Ser Asp Ser Ala Ala Ala Ala Ala Ala Ala Ala Ala
            20                  25                  30

Ala Ala Ala
        35

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly Ala Gly Gly Ser Gly Gly Tyr Gly Gly Tyr Gly Gly Tyr Gly
1               5                   10                  15

Ser Asp Ser Ala Ala Ala Ala Ala Ala Ala Ala Ala Ala Ala Ala
            20                  25                  30

<210> SEQ ID NO 49
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ser Gly Ala Gly Gly Ala Gly Gly Tyr Gly Trp Gly Asp Gly
1               5                   10                  15

Gly Tyr Gly Ser Asp Ser Ala Ala Ala Ala Ala Ala Ala Ala Ala Ala
            20                  25                  30

Ala Ala

<210> SEQ ID NO 50
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Gly Ala Gly Gly Arg Gly Asp Gly Tyr Gly Ser Gly Ser
1               5                   10                  15

Ser Ala Ala Ala Ala Ala Ala Ala Ala Ala Ala
            20                  25

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Arg Ala Gly His Asp Arg Ala Ala Gly Ser Ala Ala Ala Ala Ala

```
1               5                   10                  15

Ala Ala Ala Ala Ala Ala Ala Ala
            20

<210> SEQ ID NO 52
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Gly Ala Gly Gly Ser Gly Gly Gly Tyr Gly Trp Gly Asp Gly
1               5                   10                  15

Tyr Gly Ser Asp Ser Ala Ala Ala Ala Ala Ala Ala Ala Ala Ala
            20                  25                  30

Ala Ala

<210> SEQ ID NO 53
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 54
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Gly Ala Gly Gly Ala Gly Gly Val Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala
        35

<210> SEQ ID NO 55
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25
```

```
<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Ala Gly Gly Ala Gly Gly Tyr Gly Gly Tyr Gly Ser Asp Ser
1               5                   10                  15

Ala Ala Ala Ala Ala Ala Ala Ala Ala Ala Ala Ala
            20                  25

<210> SEQ ID NO 57
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala
            20                  25

<210> SEQ ID NO 58
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Arg Ala Gly His Asp Arg Ala Ala Gly Ser Ala Ala Ala Ala Ala
1               5                   10                  15

Ala Ala Ala Ala Ala Ala Ala Ala
            20

<210> SEQ ID NO 59
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Ala Gly Gly Ser Gly Gly Gly Tyr Gly Trp Gly Asp Gly Gly
1               5                   10                  15

Tyr Ser Ser Asp Ser Ala Ala Ala Ala Ala Ala Ala Ala Ala Ala Ala
            20                  25                  30

Ala Ala

<210> SEQ ID NO 60
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

-continued

```
Gly Ser Gly Ala Gly Gly Ala Gly Ala Tyr Gly Trp Gly Asp Asp
1               5                   10                  15

Gly Tyr Gly Ser Asp Ser Ala Ala Ala Ala Ala Ala Ala Ala Ala
                20                  25                  30

Ala Ala Ala
        35

<210> SEQ ID NO 61
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ser Gly Ala Gly Gly Arg Gly Gly Ala Tyr Gly Trp Gly Asp Gly
1               5                   10                  15

Gly Tyr Gly Ser Asp Ser Ala Ala Ala Ala Ala Ala Ala Ala Ala
                20                  25                  30

Ala Ala Ala
        35

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala
                20                  25

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Arg Ala Gly His Asp Arg Ala Ala Gly Ser Ala Ala Ala Ala
1               5                   10                  15

Ala Ala Ala Ala Ala Ala Ala Ala
                20

<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gly Ala Gly Gly Ser Gly Gly Ser Tyr Gly Trp Gly Asp Gly Gly
1               5                   10                  15

Tyr Gly Ser Asp Ser Ala Ala Ala Ala Ala Ala Ala Ala Ala Ala
```

20                  25                  30

Ala Ala

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gly Ala Gly Gly Ser Gly Gly Tyr Gly Gly Tyr Gly Gly Tyr Gly
1               5                   10                  15

Gly Tyr Gly Ser Asp Ser Ala Ala Ala Ala Ala Ala Ala Ala Ala
            20                  25                  30

Ala Ala Ala Ala Ala
        35

<210> SEQ ID NO 66
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ser Gly Gly Gly Val Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala

<210> SEQ ID NO 67
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala
            20                  25

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Ala Gly His Asp Arg Ala Ala Gly Ser Ala Ala Ala Ala Ala
1               5                   10                  15

Ala Ala Ala Ala Ala Ala Ala Ala
            20

<210> SEQ ID NO 69

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Gly Ala Gly Gly Ala Gly Gly Tyr Gly Trp Gly Asp Gly
1               5                   10                  15

Tyr Gly Ser Asp Ser Ala Ala Ala Ala Ala Ala Ala Ala Ala
            20                  25                  30

Ala Ala

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Gly Ala Gly Gly Ala Gly Gly Gly Tyr Gly Trp Gly Asp Asp
1               5                   10                  15

Gly Tyr Gly Ser Asp Ser Ala Ala Ala Ala Ala Ala Ala Ala Ala
            20                  25                  30

Ala Ala Ala Ala Ala
        35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Gly Ala Gly Gly Arg Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala Ala Ala
        35

<210> SEQ ID NO 72
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala Ala
            20                  25                  30

<210> SEQ ID NO 73
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 73

Arg Arg Ala Gly His Asp Arg Ala Ala Gly Ser Ala Ala Ala Ala
1               5                   10                  15

Ala Ala Ala Ala Ala Ala Ala Ala
            20

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gly Ala Gly Gly Ser Gly Gly Tyr Gly Gly Tyr Gly Gly Tyr
1               5                   10                  15

Gly Ser Asp Ser Ala Ala Ala Ala Ala Ala Ala Ala Ala Ala Ala Ala
                20                  25                  30

<210> SEQ ID NO 75
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Gly Ala Gly Gly Ala Gly Gly Tyr Gly Gly Tyr Gly Gly Tyr
1               5                   10                  15

Gly Ser Asp Ser Ala Ala Ala Ala Ala Ala Ala Ala Ala Ala Ala Ala
                20                  25                  30

Ala

<210> SEQ ID NO 76
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Gly Ala Gly Gly Val Gly Gly Gly Tyr Gly Trp Gly Asp Gly
1               5                   10                  15

Gly Tyr Gly Ser Asp Ser Ala Ala Ala Ala Ala Ala Ala Ala Ala Ala
                20                  25                  30

Ala Ala Ala
        35

<210> SEQ ID NO 77
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

```
Gly Ser Gly Ala Gly Gly Arg Gly Asp Gly Tyr Gly Ser Gly Ser
1               5                   10                  15

Ser Ala Ala Ala Ala Ala Ala Ala Ala Ala Ala
            20                  25
```

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Arg Arg Ala Gly His Glu Arg Ala Ala Gly Ser Ala Ala Ala Ala
1               5                   10                  15

Ala Ala Ala Ala Ala Ala Ala Ala
            20
```

<210> SEQ ID NO 79
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Ser Gly Ala Gly Arg Ser Gly Gly Ser Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala Ala
```

<210> SEQ ID NO 80
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ser Gly Ala Gly Gly Ser Gly Gly Tyr Gly Tyr Gly Gly Tyr Gly
1               5                   10                  15

Ser Asp Ser Ala Ala Ala Ala Ala Ala Ala Ala Ala Ala Ala Ala
            20                  25                  30
```

<210> SEQ ID NO 81
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Ser Gly Ala Gly Gly Ala Gly Gly Tyr Gly Gly Tyr Gly Gly Tyr Gly
1               5                   10                  15

Ser Tyr Gly Ser Asp Ser Ala Ala Ala Ala Ala Ala Ala Ala Ala
            20                  25                  30

Ala
```

```
<210> SEQ ID NO 82
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Gly Ala Gly Gly Val Gly Gly Tyr Gly Trp Gly Asp Gly
1               5                   10                  15

Gly Tyr Gly Ser Asp Ser Ala Ala Ala Ala Ala Ala Ala Ala
            20                  25                  30

Ala Ala

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Gly Ala Gly Gly Arg Arg Gly Tyr Gly Ala Tyr Gly Ser Asp
1               5                   10                  15

Ser Ser Ala Ala Ala Ala Ala Ala Ala Ala Ala Ala
            20                  25

<210> SEQ ID NO 84
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Gly Ala Gly Gly Ser Gly Gly Gly Tyr Gly Trp Gly Asp Gly Gly
1               5                   10                  15

Tyr Gly Asp Ser Ala Ala Ala Ala Ala Ala Ala Ala Ala Ala Ala Ala
            20                  25                  30

Ala Ala

<210> SEQ ID NO 85
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ser Gly Ala Gly Gly Ile Gly Gly Gly Phe Gly Arg Gly Asp Gly
1               5                   10                  15

Gly Tyr Gly Ser Gly Ser Ser Ala Ala Ala Ala Ala Ala Ala Ala
            20                  25                  30

Ala Ala Ala
        35

<210> SEQ ID NO 86
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 86

Arg Arg Ala Gly His Gly Arg Ser Ala Gly Ser Ala Ala Ala Ala
1               5                   10                  15

Ala Ala Ala Ala Ala Ala Ala Ala
            20

<210> SEQ ID NO 87
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ser Gly Ala Gly Gly Ser Gly Gly Ser Tyr Gly Trp Asp Tyr Glu
1               5                   10                  15

Ser Tyr Gly Ser Gly Ser Ala Ala Ala Ala Ala
            20                  25

<210> SEQ ID NO 88
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ser Gly Ala Gly Gly Ser Gly Gly Gly Tyr Gly Trp Gly Asp Gly
1               5                   10                  15

Gly Tyr Gly Ser Gly Ser Ser Ala Ala Ala Ala Ala Ala Ala Ala
            20                  25                  30

Ala Ala

<210> SEQ ID NO 89
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Ser Arg Arg Ser Gly His Asp Arg Ala Tyr Gly Ala Gly Ser Ala
1               5                   10                  15

Ala Ala Ala Ala Ala Ala Ala Ala Ala
            20                  25

<210> SEQ ID NO 90
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Ser Ser Ala Arg Gly Gly Ser Gly Phe Tyr Glu Thr His Asp Ser
1               5                   10                  15
```

```
Tyr Ser Ser Tyr Gly Ser Gly Ser Ser Ala Ala Ala Ala
            20                  25                  30
```

```
<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Ser Gly Ala Gly Gly Ala Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala
            20                  25

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Arg Ala Gly His Asp His Ala Ala Gly Ser Ser Gly Gly Gly Tyr
1               5                   10                  15

Ser Trp Asp Tyr Ser Ser Tyr Gly Ser Glu Ser Ala Ala Ala Ala
            20                  25                  30

Ala Ala Ala Ala Ala
        35

<210> SEQ ID NO 94
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Gly Ala Gly Gly Val Gly Gly Tyr Gly Gly Asp Gly
1               5                   10                  15

Gly Tyr Gly Ser Gly Ser Ser Ala Ala Ala Ala Ala Ala Ala Ala
            20                  25                  30

Ala Ala Ala
        35
```

```
<210> SEQ ID NO 95
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Ala Gly His Asp Arg Ala Ala Gly Ser Ala Ala Ala Ala Ala
1               5                   10                  15

Ala Ala Ala Ala Ala Ala Ala Ala
            20

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala Ala

<210> SEQ ID NO 97
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ser Gly Ala Gly Arg Ala Gly Gly Asp Tyr Gly Trp Gly Asp Gly
1               5                   10                  15

Gly Tyr Gly Ser Asp Ser Ala Ala Ala Ala Ala Ala Ala Ala Ala
            20                  25                  30

Ala

<210> SEQ ID NO 98
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

<210> SEQ ID NO 99
<211> LENGTH: 33
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 99

Ser Gly Ala Gly Gly Ser Gly Gly Tyr Gly Trp Gly Asp Gly Gly
1               5                   10                  15

Tyr Gly Ser Asp Ser Ala Ala Ala Ala Ala Ala Ala Ala Ala Ala
                20                  25                  30

Ala

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala
                20                  25

<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Gln Ala Gly His Glu Arg Ala Ala Gly Ser Ala Ala Ala Ala Ala
1               5                   10                  15

Ala Ala Ala Ala Ala Ala Ala Ala
                20

<210> SEQ ID NO 102
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gly Ala Gly Gly Ser Gly Arg Gly Tyr Gly Trp Gly Asp Gly Gly
1               5                   10                  15

Tyr Gly Ser Asp Ser Ala Ala Ala Ala Ala Ala Ala Ala Ala Ala
                20                  25                  30

Ala Ala

<210> SEQ ID NO 103
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ser Gly Ala Gly Gly Ala Gly Gly Asp Tyr Gly Trp Gly Asp Gly
1               5                   10                  15

```
Gly Tyr Gly Ser Asp Ser Ala Ala Ala Ala Ala Ala Ala Ala
            20                  25                  30

Ala

<210> SEQ ID NO 104
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala

<210> SEQ ID NO 105
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala
            20                  25

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Arg Ala Gly His Asp Arg Ala Ala Gly Ser Ala Ala Ala Ala Ala
1               5                   10                  15

Ala Ala Ala Ala Ala Ala Ala
            20

<210> SEQ ID NO 107
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala Ala

<210> SEQ ID NO 108
```

<211> LENGTH: 33
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Gly Ser Gly Ala Gly Gly Ala Gly Gly Asp Tyr Gly Trp Gly Asp Gly
1               5                   10                  15

Gly Tyr Gly Ser Asp Ser Ala Ala Ala Ala Ala Ala Ala Ala Ala
            20                  25                  30

Ala

<210> SEQ ID NO 109
<211> LENGTH: 33
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Ser Gly Ala Gly Gly Ala Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala

<210> SEQ ID NO 110
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala
            20                  25

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Arg Arg Ala Gly His Asp Arg Ala Ala Gly Ser Ala Ala Ala Ala Ala
1               5                   10                  15

Ala Ala Ala Ala Ala Ala Ala Ala
            20

<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 112

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala
            20                  25                  30

Ala Ala

<210> SEQ ID NO 113
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Ser Gly Ala Gly Gly Ala Gly Gly Asp Tyr Gly Trp Gly Asp Gly
1               5                   10                  15

Gly Tyr Gly Ser Asp Ser Ala Ala Ala Ala Ala Ala Ala Ala Ala Ala
            20                  25                  30

Ala

<210> SEQ ID NO 114
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala Ala
            20                  25                  30

Ala

<210> SEQ ID NO 115
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ser Gly Ala Gly Gly Arg Gly Asp Gly Tyr Gly Ser Gly Ser
1               5                   10                  15

Ser Ala Ala Ala Ala Ala Ala Ala Ala Ala Ala Ala Ala
            20                  25

<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Arg Ala Gly His Asp Arg Ala Ala Gly Ser Ala Ala Ala Ala Ala
1               5                   10                  15
```

Ala Ala Ala Ala Ala Ala Ala
            20

<210> SEQ ID NO 117
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Gly Ala Gly Gly Ser Gly Gly Tyr Gly Trp Gly Asp Gly Gly
1               5                   10                  15

Tyr Gly Ser Asp Ser Ala Ala Ala Ala Ala Ala Ala Ala Ala
            20                  25                  30

Ala Ala

<210> SEQ ID NO 118
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Ser Gly Ala Gly Gly Ala Gly Gly Asp Tyr Gly Trp Gly Asp Gly
1               5                   10                  15

Gly Tyr Gly Ser Asp Ser Ala Ala Ala Ala Ala Ala Ala Ala
            20                  25                  30

Ala

<210> SEQ ID NO 119
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Gly Ala Gly Gly Ala Gly Gly Tyr Gly Trp Gly Asp Gly Gly
1               5                   10                  15

Tyr Gly Ser Asp Ser Ala Ala Ala Ala Ala Ala Ala Ala Ala
            20                  25                  30

Ala

<210> SEQ ID NO 120
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala
            20                  25

<210> SEQ ID NO 121

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Arg Ala Gly His Asp Arg Ala Ala Gly Ser Ala Ala Ala Ala
1               5                   10                  15

Ala Ala Ala Ala Ala Ala Ala Ala
            20

<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Gly Ala Gly Gly Ser Gly Gly Tyr Gly Trp Gly Asp Gly Gly
1               5                   10                  15

Tyr Gly Ser Asp Ser Ala Ala Ala Ala Ala Ala Ala Ala Ala
            20                  25                  30

Ala Ala

<210> SEQ ID NO 123
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Ser Gly Ala Gly Gly Val Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala
        35

<210> SEQ ID NO 124
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Gly Ala Gly Gly Ala Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 125

Ser Ser Gly Ala Gly Gly Ala Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala

<210> SEQ ID NO 126
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ser Gly Ala Gly Gly Arg Gly Asp Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Gly Ala Gly Gly Ser Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala Ala

<210> SEQ ID NO 128
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Ser Gly Ala Gly Gly Val Gly Gly Gly Tyr Gly Trp Gly Asp Gly
1               5                   10                  15

Gly Tyr Gly Ser Asp Ser Ala Ala Ala Ala Ala Ala Ala Ala Ala Ala
            20                  25                  30

Ala Ala Ala
        35

<210> SEQ ID NO 129
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Gly Ala Gly Gly Ala Gly Gly Tyr Gly Gly Tyr Gly Ser Asp Ser

```
                1               5                  10                  15
Ala Ala Ala Ala Ala Ala Ala Ala Ala Ala Ala
                20                  25

<210> SEQ ID NO 130
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Ser Gly Ala Gly Gly Ala Gly Gly Tyr Gly Trp Gly Asp Gly
1               5                  10                  15

Gly Tyr Gly Ser Asp Ser Ala Ala Ala Ala Ala Ala Ala Ala Ala
                20                  25                  30

Ala Ala Ala
        35

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Gly Ala Gly Gly Arg Gly Asp Gly Gly Tyr Gly Ser Gly Ser Ser
1               5                  10                  15

Ala Ala Ala Ala Ala Ala Ala Ala Ala Ala Ala Ala
                20                  25

<210> SEQ ID NO 132
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Arg Ala Gly Tyr Asp Arg Ala Ala Gly Ser Ala Ala Ala Ala
1               5                  10                  15

Ala Ala Ala Ala Ala Ala Ala Ala
                20

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gly Ala Gly Gly Ser Gly Gly Tyr Gly Trp Gly Asp Gly Gly
1               5                  10                  15

Tyr Gly Ser Asp Ser Ala Ala Ala Ala Ala Ala Ala Ala Ala Ala
                20                  25                  30

Ala Ala
```

```
<210> SEQ ID NO 134
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Gly Ala Gly Gly Ala Gly Gly Tyr Gly Gly Tyr Gly Ser Asp
1               5                   10                  15

Ser Ala Ala Ala Ala Ala Ala Ala Ala Ala Ala Ala Ala Ala Ala
            20                  25                  30

<210> SEQ ID NO 135
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Ser Gly Ala Gly Gly Ala Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala
        35

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Gly Ala Gly Gly Arg Gly Asp Gly Gly Tyr Gly Ser Gly Ser Ser
1               5                   10                  15

Ala Ala Ala Ala Ala Ala Ala Ala Ala Ala Ala Ala
            20                  25

<210> SEQ ID NO 137
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Arg Ala Gly Tyr Asp Arg Ala Ala Gly Ser Ala Ala Ala Ala Ala
1               5                   10                  15

Ala Ala Ala Ala Ala Ala Ala Ala
            20

<210> SEQ ID NO 138
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 138

Ser Gly Ala Gly Gly Ser Gly Gly Tyr Gly Trp Gly Asp Gly Gly
1               5                   10                  15

Tyr Gly Ser Asp Ser Ala Ala Ala Ala Ala Ala Ala Ala Ala
                20                  25                  30

Ala Ala

<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Gly Ala Gly Gly Ala Gly Gly Tyr Gly Gly Tyr Gly Ser Asp
1               5                   10                  15

Ser Ala Ala Ala Ala Ala Ala Ala Ala Ala Ala Ala Ala
                20                  25                  30

<210> SEQ ID NO 140
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Ser Gly Ala Gly Gly Ala Gly Gly Tyr Gly Trp Gly Asp Gly
1               5                   10                  15

Gly Tyr Gly Ser Asp Ser Ala Ala Ala Ala Ala Ala Ala Ala Ala
                20                  25                  30

Ala Ala

<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala
                20                  25                  30

<210> SEQ ID NO 142
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Arg Ala Gly His Asp Arg Ala Ala Gly Ser Ala Ala Ala Ala
1               5                   10                  15

Ala Ala Ala Ala Ala Ala Ala Ala
                20
```

<210> SEQ ID NO 143
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Gly Ala Gly Gly Ser Gly Gly Gly Tyr Gly Trp Gly Asp Gly
1               5                   10                  15

Tyr Gly Ser Asp Ser Ala Ala Ala Ala Ala Ala Ala Ala Ala Ala
            20                  25                  30

Ala Ala

<210> SEQ ID NO 144
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Ser Gly Ala Gly Gly Ala Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Gly Ala Gly Gly Thr Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

<210> SEQ ID NO 146
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Gly Ala Gly Gly Ala Gly Gly Gly Tyr Gly Trp Gly Asp Gly Gly
1               5                   10                  15

Tyr Gly Ser Asp Ser Ala Ala Ala Ala Ala Ala Ala Ala Ala Ala
            20                  25                  30

Ala

<210> SEQ ID NO 147
<211> LENGTH: 30
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 147

Gly Ser Gly Ala Gly Gly Arg Gly Asp Gly Tyr Gly Ser Gly Ser
1               5                   10                  15

Ser Ala Ala Ala Ala Ala Ala Ala Ala Ala Ala Ala Ala Ala Ala
            20                  25                  30

<210> SEQ ID NO 148
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Arg Ala Gly His Asp Arg Ala Ala Gly Ser Ala Ala Ala Ala
1               5                   10                  15

Ala Ala Ala Ala Ala Ala Ala Ala Ala
            20

<210> SEQ ID NO 149
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Gly Ala Gly Gly Ser Gly Gly Gly Tyr Gly Trp Gly Asp Gly Gly
1               5                   10                  15

Tyr Gly Ser Asn Ser Ala Ala Ala Ala Ala Ala Ala Ala Ala Ala
            20                  25                  30

Ala Ala

<210> SEQ ID NO 150
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Ser Gly Ala Gly Gly Val Gly Gly Gly Tyr Gly Trp Gly Asp Gly
1               5                   10                  15

Gly Tyr Gly Ser Asp Ser Ala Ala Ala Ala Ala Ala Ala Ala Ala
            20                  25                  30

Ala Ala Ala
        35

<210> SEQ ID NO 151
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151
```

```
Gly Ser Gly Ala Gly Gly Ala Gly Gly Tyr Gly Trp Gly Asp Gly
1               5                   10                  15

Gly Tyr Gly Ser Asp Ser Ala Ala Ala Ala Ala Ala Ala Ala
            20                  25                  30

Ala Ala

<210> SEQ ID NO 152
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ser Gly Ala Gly Gly Arg Gly Asp Gly Tyr Gly Ser Gly Ser
1               5                   10                  15

Ser Ala Ala Ala Ala Ala Ala Ala Ala Ala Ala Ala Ala Ala
            20                  25

<210> SEQ ID NO 153
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Arg Arg Ala Gly His Asp Arg Ala Ala Gly Ser Ala Ala Ala Ala
1               5                   10                  15

Ala Ala Ala Ala Ala Ala Ala Ala
            20

<210> SEQ ID NO 154
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Gly Ala Gly Gly Ser Gly Gly Gly Tyr Gly Trp Gly Asp Gly
1               5                   10                  15

Tyr Gly Ser Asp Ser Ala Ala Ala Ala Ala Ala Ala Ala Ala Ala
            20                  25                  30

Ala Ala

<210> SEQ ID NO 155
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Ser Gly Ala Gly Gly Ala Gly Gly Asp Tyr Gly Trp Gly Asp Gly
1               5                   10                  15

Gly Tyr Gly Ser Asp Ser Ala Ala Ala Ala Ala Ala Ala Ala Ala
            20                  25                  30
```

-continued

Ala

<210> SEQ ID NO 156
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 157
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Ser Gly Ala Gly Gly Ala Gly Gly Asp Tyr Gly Trp Gly Asp Gly
1               5                   10                  15

Gly Tyr Gly Ser Asp Ser Ala Ala Ala Ala Ala Ala Ala Ala Ala
            20                  25                  30

Ala

<210> SEQ ID NO 158
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Gly Ala Gly Gly Ser Gly Gly Tyr Gly Gly Tyr Gly Ser Asp Ser
1               5                   10                  15

Ala Ala Ala Ala Ala Ala Ala Ala Ala Ala Ala Ala Ala
            20                  25

<210> SEQ ID NO 159
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Ser Gly Ala Gly Gly Val Gly Gly Gly Tyr Gly Trp Gly Asp Gly
1               5                   10                  15

Gly Tyr Gly Gly Tyr Gly Ser Asp Ser Ala Ala Ala Ala Ala Ala
            20                  25                  30

Ala Ala Ala Ala
        35

<210> SEQ ID NO 160
<211> LENGTH: 34
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 160

Gly Ser Gly Ala Gly Gly Val Gly Gly Gly Tyr Gly Arg Gly Asp Ser
1               5                   10                  15

Gly Tyr Gly Ser Gly Ser Ser Ala Ala Ala Ala Ala Ala Ala Ala
            20                  25                  30

Ala Ala

<210> SEQ ID NO 161
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Arg Ala Gly His Asp Arg Ser Ser Gly Ser Ala Ala Ala Ala Ala
1               5                   10                  15

Ala Ala Ala Ala Ala Ala Ala Ala
            20

<210> SEQ ID NO 162
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Gly Ala Gly Gly Ser Gly Gly Gly Tyr Gly Trp Asp Tyr Gly Ser
1               5                   10                  15

Tyr Gly Ser Asp Ser Ala Ala Ala Ala Ala Ala Ala Ala Ala Ala Ala
            20                  25                  30

Ala

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Ser Gly Ala Gly Gly Ser Gly Gly Tyr Gly Trp Asp Tyr Gly
1               5                   10                  15

Gly Tyr Gly Ser Asp Ser Ala Ala Ala Ala Ala Ala Ala Ala Ala Ala
            20                  25                  30

Ala Ala

<210> SEQ ID NO 164
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 164

Gly Ser Gly Ala Gly Gly Ser Gly Gly Gly Tyr Gly Trp Asp Gly
1               5                   10                  15

Gly Tyr Gly Ser Asp Ser Ala Ala Ala Ala Ala Ala Ala Ala Ala
                20                  25                  30

Ala Ala

<210> SEQ ID NO 165
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Ser Gly Ala Gly Gly Arg Gly Asp Gly Gly Tyr Gly Ser Gly Ser
1               5                   10                  15

Ser Ala Ala Ala Ala Ala Ala Ala Ala Ala Ala Ala Ala
                20                  25

<210> SEQ ID NO 166
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Arg Ala Gly His Asp His Ala Ala Gly Ser Ser Gly Gly Tyr
1               5                   10                  15

Ser Trp Asp Tyr Ser Ser Tyr Gly Ser Glu Ser Ala Ala Ala Ala Ala
                20                  25                  30

Ala Ala Ala Ala Ala
            35

<210> SEQ ID NO 167
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Ser Gly Ala Gly Gly Val Gly Gly Tyr Gly Gly Gly Asp Gly
1               5                   10                  15

Gly Tyr Gly Ser Gly Ser Ser Ala Ala Ala Ala Ala Ala Ala Ala
                20                  25                  30

Ala Ala Ala
        35

<210> SEQ ID NO 168
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Arg Arg Ala Gly His Asp Arg Ala Tyr Gly Ala Gly Ser Ala Ala
```

Ala Ala Ala Ala Ala Ala Ala
            20

<210> SEQ ID NO 169
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Ala Ala Ala Ala Ala Ala Ala Ala Gly Ser Gly Ala Gly Gly Arg
1               5                   10                  15

Gly Asp Gly Gly Tyr Gly Ser Gly Ser Ser Ala Ala Ala
            20                  25

<210> SEQ ID NO 170
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ala Ala Ala Ala Ala Ala Ser Gly Ala Gly Gly Ser Gly Gly Gly
1               5                   10                  15

Tyr Gly Trp Gly Asp Gly Gly Tyr Gly Ser Asp Ser Ala Ala Ala Ala
            20                  25                  30

<210> SEQ ID NO 171
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Gly Gly Ala Gly Gly Gly Tyr Gly Trp Gly Asp Gly Gly Tyr Gly
1               5                   10                  15

Ser Asp Ser Ala Ala Ala Ala
            20

<210> SEQ ID NO 172
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Ala Ala Ala Ala Ala Ala Ala Ala Ser Gly Ala Gly Gly Ser Gly
1               5                   10                  15

Gly Tyr Gly Gly Tyr Gly Gly Tyr Gly Ser Asp Ser Ala Ala Ala Ala
            20                  25                  30

<210> SEQ ID NO 173
<211> LENGTH: 29
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 173

Ala Ala Ala Ala Ala Ala Ala Ala Gly Ser Gly Ala Gly Gly Arg
1               5                   10                  15

Gly Asp Gly Gly Tyr Gly Ser Gly Ser Ser Ala Ala Ala
                20                  25

<210> SEQ ID NO 174
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Ala Ala Ala Ala Ala Ala Ser Gly Ala Gly Gly Ser Gly Gly
1               5                   10                  15

Tyr Gly Trp Gly Asp Gly Gly Tyr Gly Ser Asp Ser Ala Ala Ala Ala
                20                  25                  30

<210> SEQ ID NO 175
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Ala Ala Ala Ala Ala Ala Ala Ala Ser Gly Ala Gly Gly Ser Gly
1               5                   10                  15

Gly Tyr Gly Gly Tyr Gly Ser Asp Ser Ala Ala Ala Ala
                20                  25

<210> SEQ ID NO 176
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Ala Ala Ala Ala Ala Ala Ala Ala Ala Ser Gly Ala Gly Gly Ala
1               5                   10                  15

Gly Gly Tyr Gly Gly Tyr Gly Ser Asp Ser Ala Ala Ala Ala
                20                  25                  30

<210> SEQ ID NO 177
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ala Ala Ala Ala Ala Ala Ala Gly Ser Gly Ala Gly Gly Arg Gly
1               5                   10                  15

Asp Gly Gly Tyr Gly Ser Gly Ser Ser Ala Ala Ala Ala
                20                  25
```

<210> SEQ ID NO 178
<211> LENGTH: 34
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Ala Ala Ala Ala Ala Ala Ala Ser Gly Ala Gly Gly Ala Gly Gly Gly
1               5                   10                  15

Tyr Gly Trp Gly Asp Gly Gly Tyr Ser Ser Asp Ser Ala Ala Ala Ala
            20                  25                  30

Ala Ala

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Ala Gly Gly Ala Gly Gly Gly Tyr Gly Trp Gly Asp Asp Gly Tyr Gly
1               5                   10                  15

Ser Asp Ser Ala Ala Ala Ala
            20

<210> SEQ ID NO 180
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Ala Gly Gly Arg Gly Gly Gly Tyr Gly Trp Gly Asp Gly Gly Tyr Gly
1               5                   10                  15

Ser Asp Ser Ala Ala Ala Ala
            20

<210> SEQ ID NO 181
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Ala Ala Ala Ala Ala Ala Ala Ala Gly Ser Gly Ala Gly Gly Arg Gly
1               5                   10                  15

Asp Gly Gly Tyr Gly Ser Gly Ser Ser Ala Ala Ala
            20                  25

<210> SEQ ID NO 182
<211> LENGTH: 31
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 182

Ala Ala Ala Ala Ala Ala Ser Gly Ala Gly Gly Ser Gly Gly Ser Tyr
1               5                   10                  15

Ser Trp Gly Asp Gly Gly Tyr Gly Ser Asp Ser Ala Ala Ala Ala
            20                  25                  30

<210> SEQ ID NO 183
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ala Ala Ser Gly Ala Gly Gly Ser Gly Gly Tyr Gly Gly Tyr Gly
1               5                   10                  15

Gly Tyr Gly Gly Tyr Gly Ser Asp Ser Ala Ala Ala Ala
            20                  25

<210> SEQ ID NO 184
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Gly Gly Val Gly Gly Gly Tyr Gly Trp Gly Asp Gly Gly Tyr Gly
1               5                   10                  15

Ser Asp Ser Ala Ala Ala Ala
            20

<210> SEQ ID NO 185
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Ala Ala Ala Ala Ala Ala Gly Ser Gly Ala Gly Gly Arg Gly
1               5                   10                  15

Asp Gly Gly Tyr Gly Ser Gly Ser Ser Ala Ala Ala
            20                  25

<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ala Ala Ala Ala Ala Ala Ser Gly Ala Gly Gly Ala Gly Gly
1               5                   10                  15

Tyr Gly Trp Gly Asp Gly Gly Tyr Gly Ser Asp Ser Ala Ala Ala Ala
            20                  25                  30

<210> SEQ ID NO 187
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Gly Gly Ala Gly Gly Gly Tyr Gly Trp Gly Asp Asp Gly Tyr Gly
1               5                   10                  15

Ser Asp Ser Ala Ala Ala Ala
            20
```

COMPOSITE MATERIALS

This application is a continuation of International Application No. PCT/EP2005/002473, filed Mar. 4, 2005, which claims priority of British Application No. 0405045.6, filed Mar. 5, 2004.

FIELD OF THE INVENTION

The invention relates to a composite material comprising one or more silk elements in an acrylic or cross-lined protein matrix, its method of manufacture and its use in surgical implants.

BACKGROUND

Biodegradable polymer materials made of silk fibroin elements are known, for example, from US-A-2004/0005363 (Tsukada et al.). This patent document teaches a composite material made from silk fibroin and another secondary substance, such as cellulose, chitin, chitosan (or derivatives), Keratin or polyvinyl alcohol. The composite material can be used as a sustained release substrate for medicines, a biological cell growth substrate, a metal ion-absorbing material and a biodegradable water-absorbing material.

Another example of a composite material in which proteins coat the surface of a surgical device is disclosed in WO-A-94/22584 entitled "Chronic Endothelial Cell Culture under flow". In this patent application, the inner lumen of a hollow polypropylene fibre was coated with a synthetic protein polymer Fibronectin F which contains multiple repeats of the RGD fibronectin binding site. This produced an inner lumen surface which was substantially uniformly coated with the synthetic protein polymer on which cells could be grown. The polypropylene fibres can be used in vascular grafts. The strength of the vascular graft is as a result dependent on the tensile strength of the polypropylene fibres.

The surgical device (stent grafts and vascular grafts) described in WOA-01/38373 (Boston Scientific) exploits the strength of spider silk by providing an outer or interstitial sheath over the outside surface or the luminal surface of an inner stent. The inner stent is made from a multitude of materials such as synthetic textile materials, fluoropolymers and polyolefines. Nylon, polyester and polyurethane are often used. These-materials which can not be resorbed by the body. The material of the outer sheath is non-resorbable conventional man-made polymeric material or a combination of spider silk and man made polymeric material.

SUMMARY OF THE INVENTION

These and other objects of the invention are solved by providing a composite material having one or more silk elements in an acrylic or cross-linked protein matrix. This material is highly biocompatible. Preferably the silk elements are made from wild silkworm silk, domestic silkworm silk spider-dragline silk, and filaments spun from recombinant silk protein or protein analogues or mixtures of these. A protein matrix is preferred because this means that both the protein matrix and the silk elements are resorbable.

In one embodiment of the invention, the silk elements are embedded in an acrylic matrix made of a cyanoacrylate, as this acrylate is known to be biocompatible. Alternatively, the silk elements can be incorporated into a matrix made of cross-linked fibroin or cross-linked casein.

In a particularly advantageous embodiment of the invention, the silk elements are made from the silk derived from wild silkworms (i.e. Tussah silk) as the resorbtion rate of the composite material formed from the cross-lined protein matrix and wild silkworm silk elements is slower than that of composite material with silk elements derived from spider silk.

In one embodiment of the invention, the silk elements formed from a plurality of short filaments with a staple-length less than 120 mm are from carded filaments (i.e. filaments drawn to lie approximately parallel to one another by a combing process). In another embodiment of the invention, the silk elements are twisted into a thread which can also be further twisted into a cord or rope or woven, braided, embroidered, wound, stitched or knitted.

The composite material can be formed into a substantially cylindrical form with the silk elements wound at an angle in excess of 40 degrees to the long axis of the substantially cylindrical form or circumferentially to the long axis. On a luminal surface of the form, the silk elements can be wound parallel to the long axis of the substantially cylindrical form. This latter construction has the advantage that it should stimulate longitudinal movement of nerve processes in a sleeve and therefore promote nerve regeneration.

Mineralisation of the composite material is advantageous as this allows the composite material to be used as a bone substitute and stimulates regrowth of the bone material.

The principal silk protein used in the silk elements contains at least eight repeats of the triplet RGD. The eight repeats of the triplet RGD are located immediately adjacent to turns or predicted turns of a structure of the principal silk protein. This is advantageous as this sequence when next to a turn specifically recognises and holds the fibronectin binding site of integrin molecules anchored to the surface of most metazoan cell types. In turn this leads to excellent cell adhesion and advantageous changes in cell physiology including polarisation of function, cell differentiation and changes in the cell cycle.

The composite material is in one use formed into surgically implantable devices, such as sutures, artificial ligaments and tendons, endoluminar devices, anastomosis devices, and sleeves to aid in the regeneration of nerve cells The invention also comprises a method for the manufacture of a compound material with a first step of providing one or more silk elements and a second step of embedding the silk element in an acrylic or protein matrix. The silk elements can be obtained by degumming and unwinding or combing silk from a cocoon.

Fibroin can be prepared for the protein matrix by dissolving domestic or wild silkworm silk or cocoons in one or more chaotropic agents, such as calcium nitrate solution and lithium thiocyanate solution.

The protein matrix is cross-linked using a cross-linking agent such as formaldehyde vapour, glutaraldehyde, polyglutaraldehyde, carbodiimide and genipin.

The acrylic or fibroin material is applied to the silk elements by dipping, painting, spraying or casting.

An apparatus for the manufacture of an object made from the composite material is also part of the invention. The apparatus has a storage region having silk elements, a substantially cylindrical former and finally a feeding means to place said silk elements about the former.

The feeding means comprises rollers and tension is maintained between the rollers and the former to pre-stress and straighten the silk elements so as to ensure a good final product.

In one embodiment of the invention, a take up drum is used to form an object which is then removed as a substantially cylindrical form from the take up drum. Advantageously, cared silk fibres are fed to a cylindrical former and continuously coated onto the substantially cylindrical drum and finally a composite sheet emerges continuously from the substantially cylindrical drum.

DESCRIPTION OF THE DRAWINGS

FIGS. 4(A-C) show the distribution of the fibronectin binding triplet RGD in the repetitive part of the sequence of *Antheraea pernyi* (left column) and *A. yamamai* (right column) heavy chain fibroin (SEQ ID NOS: 11-168 are disclosed respectively in order of appearance).

FIG. 5 shows the consensus repeat sequence for the glycine-rich domains for the first 900 repetitive amino acids of the repetitive region of *A. pernyii* heavy chain fibroin (SEQ ID NOS 169-187 are disclosed respectively in order of appearance).

FIG. 6 shows the position of a putative turn immediately adjacent to the RGD triplet in the consensus sequence from the glycine-rich domain of *A. pernyi* heavy chain fibroin (SEQ ID NO: 7).

DETAILED DESCRIPTION OF THE INVENTION

Figure 1:
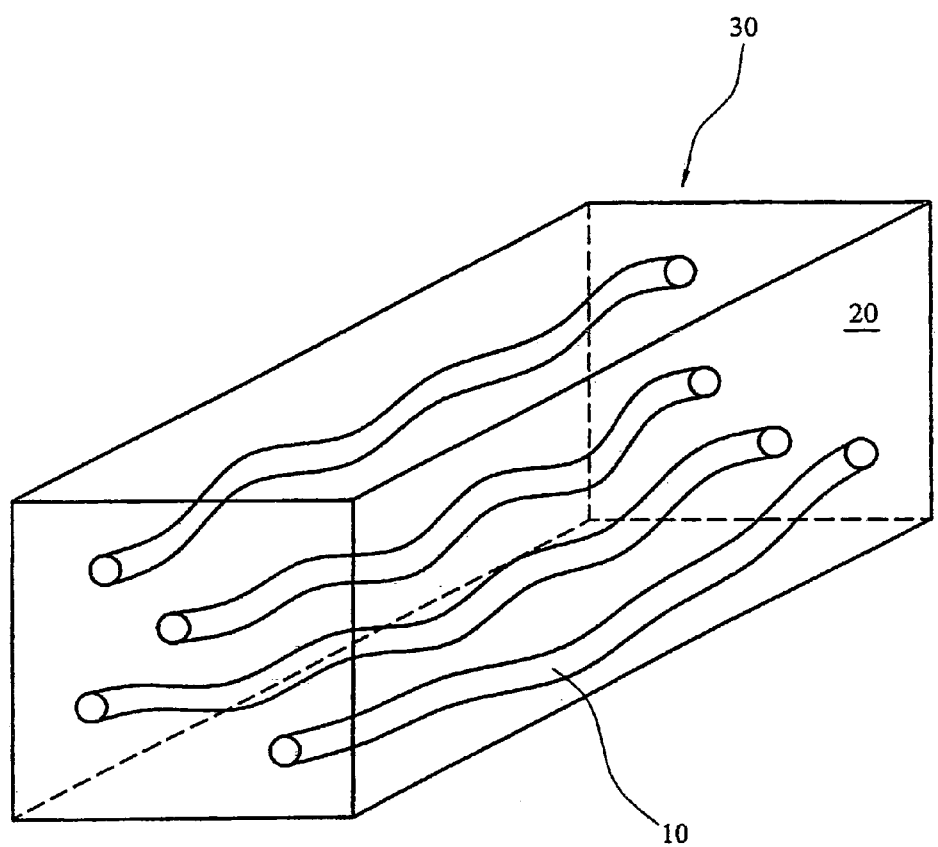
FIG. 1 shows a composite material according to this invention.

FIG. 1 shows a composite material 30 comprising one or more silk elements 10 in a matrix material 20. The matrix material 20 can be an acrylic matrix, made for example from a cyanoacrylate, or a protein matrix. The protein matrix can, for example, be a fibroin matrix or a casein matrix. Other highly soluble proteins could also be used. The protein matrix is cross-lined using a cross-liking agent such as formaldehyde vapour glutaraldehyde, polyglutaraldehyde, formaldehyde carbodiimide and genipin. In one embodiment the protein matrix is cross-lined by heating substantially dry formaldehyde vapour generated by heating paraformaldehyde in a sealed container to 80-100 degrees centigrade for 5 minutes to 3 hours.

The silk elements 10 are made from domestic silkworm soil, wild silkworm silk or spider dragline silk. The silk elements 10 could also be made from recombinant silk protein or protein analogues. The silk elements 10 produced from wild silkworm in general means those elements produced by *Antheraea pernyi, Antheraea yamamai, Antheraea militta, Antheraea assama, Philosamia Cynthia ricini* and *Philosamia Cynthia pryeri*. The silk of other Saturnid moths such as those of the genus Actias or Cecropia though not generally defined as wild silk worms yield a closely similar silk element and can be used in this invention as the silk elements 10.

In FIG. 1 a simple block of composite material 30 is known. However, other shapes are possible such as fibres, rods, sheets or tubes as will become clear from the discussion below.

The silk elements 10 can be made up of a plurality of silk elements which have been twisted together to form a thread. The silk elements 10 can be further made of a plurality of short filaments of silk, for example with a staple length as long as possible and at least 20 mm. The silk elements 10 can be twisted into pairs or multiples to form a thread which can also be further twisted into a cord or rope or woven, braided, embroidered, wound, stitched or knitted to form devices. In one advantageous embodiment of the invention, the silk elements 10 comprise carded filaments.

In one embodiment of the invention, the silk elements 10 are degummed from the silk cocoon. However, other methods of extracting the silk elements 10 can be used.

The fibroin for the protein matrix 20 is extracted by dissolving domestic or wild silkworm silk or cocoons in one or more chaotropic agents, such as calcium nitrate solution and lithium thiocyanate solution. In the case of wild sills, it is necessary to heat the chaotropic agent. The silk elements 10 are placed in the resultant solution-which is then dialysed to remove the chaotropic agent or agents and concentrated or dried by evaporation or reverse dialysis. The concentrated fibroin solution can be dried into films or flakes for storage and redissolved in distilled water or other solvents when required.

U.S. Pat. No. 5,245,012 (US Army) also teaches a method of dissolving silk protein extracted from different arachnid species using varying solvent systems. The teachings of this patent are incorporated herein by reference.

Figure 2:
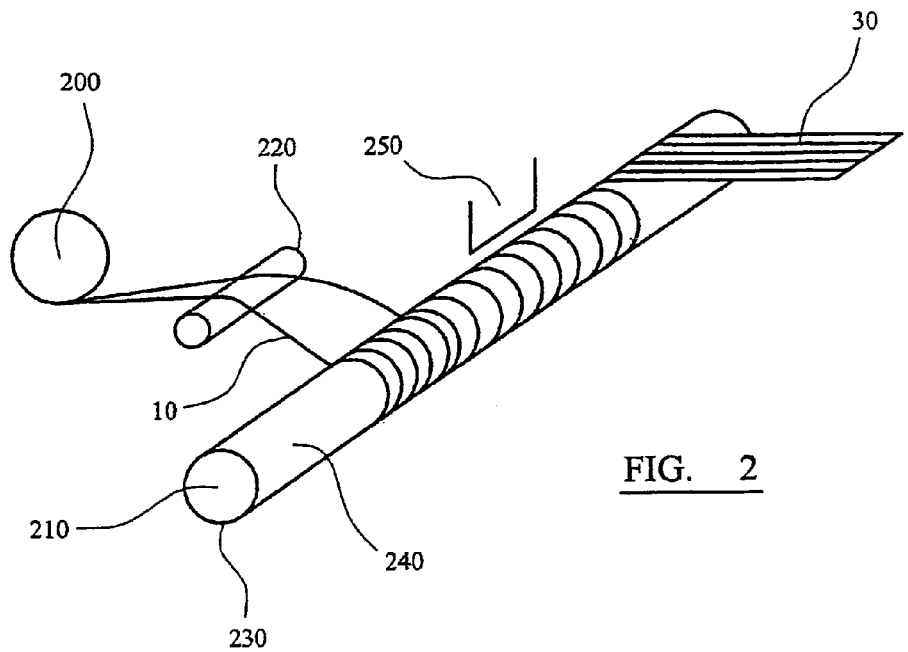
FIG. 2 shows a first manufacturing method for the composite material.

The composite material 30 of the invention can be used to make a variety of objects. One example of an apparatus for the manufacture of the objects 100 is shown in FIG. 2 in which the silk elements 10 are initially held in a storage region 200 and are spooled (or otherwise fed) to a drum 210 over rollers 220 and wrapped circumferentially or helically about the drum 210. The function of the rollers 220 is to ere that the silk elements 10 are pre-stressed and therefore firmly placed on the drum 210. The matrix material 20 is then coated by an application device 250 over the outer surface 240 of the drum 210 with matrix material 20 to affix and embed the silk elements 10. It will be understood that the drum 210 could also be a mandrel or more generally a former. It will be understood that the silk elements 10 can be laid down on the drum 210 or mandrel in many different patterns of orientation by rotating the drum 210 or mandrel and changing the spatial relationship between the drum 210 and the rollers 220.

In a further embodiment a composite rope or cable structure is formed as follows. Two or more lengths of single, double or multiple ply silk threads are twisted into a thin rope. The acrylate or fibroin solutions for the matrix can be applied before or after twisting. After drying or partial drying, the matrix is then cross-linked by chemical treatment, preferably by hot formaldehyde vapour. It will be understood that by successive twisting varying hierarchical levels of construction to give cords, ropes or cables of thicknesses appropriate to end use. The resulting materials can be incorporated into a variety of prosthetic devices including-tendon and ligament prostheses or embroidered or knitted devices.

The object 30 constructed in accordance with the teas of FIG. 2 can be advantageously made with silk elements 10 formed from carded silk filaments derived from silk brins. Carded silk filaments are very thin (30 µm diameter) allowing the manufacture of thin-walled devices or composite sheets.

The drum 210 can be so arranged that a continuous sheet made of composite material 30 emerges from the drum 210 as shown in the FIG. 2.

As the composite material 30 is biocompatible, it can be used to make an implant, such as an endolumnal device, a stent device, an anastomosis is device, a sure, or a device to promote nerve regeneration. It is known that the silk elements 10 provide an excellent substrate for cell or tissue growth. Therefore some of the matrix material 20 of the object 100 can be abraded away to reveal some of the silk elements 10 on either an inner (or endolumnal) surface 230 of the object 30 or on an outer surface 240 of the object 30.

Figure 3:
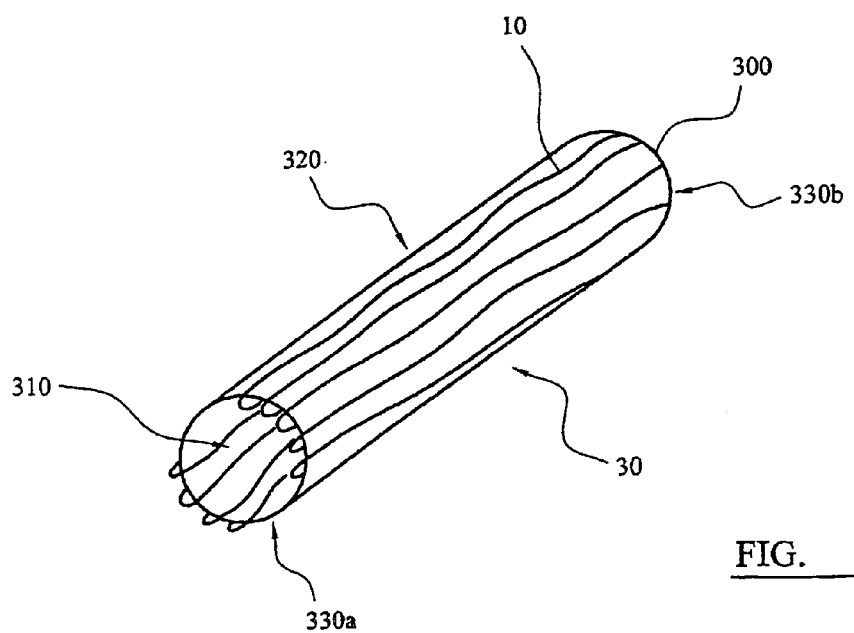
FIG. 3 shows a second manufacturing method for the composite material.

Another method for the manufacture of the object 30 in a tubular structure is shown in FIG. 3 in which silk elements 10 are wrapped substantially longitudinally along the surface of a former 300 on both an inner surface 310 and an outersurface 320 of the former 300. The former has typically a diameter between 0.5 mm but can have a diameter up to 10 m and has a long axis 325. The former 300 could also be tapered. The matrix material 20 is applied over the silk elements 10 and allowed to dry and thus embed the silk elements 10 in the object. Application of the materials by dipping, painting, spraying or casting. The ends 330a and 330b of the object 30 can be cut away and the former 300 slipped out. A tubular object is thus created. Formers coated with a layer of wax or which can be caused to collapse into a smaller diameter can be used to facilitate removal of the object 30 from the former 300.

EXAMPLES

Example 1

Preparation of Composite Materials from Carded *Antheraea pernyii* Silk Filaments

*Antheraea pernyii* silk filaments prepared from degummed silk cocoons were obtained from a commercial supplier. The carded silk from the sepin was smoothed into flat sheets and gently tensioned to pull the silk filaments parallel. Keeping the silk tensioned they were wound on to cylindrical formers 0.25 mm to 30 mm in diameter. The largest cylinders were made of glass and had a substantially smooth surface. The smallest cylinders 0.25 mm were prepared by coating a thin stiff wire in low melting point wax. Cylindrical formers with intermediate diameters were made from low melting point wax. The silk filaments were generally laid circumferentially on the largest formers but were laid in a helical fashion on the smaller cylindrical formers.

Care was taken to ensure a uniform dense lay of filaments was achieved on the cylindrical formers. The silk filaments at the ends of the thin cylindrical formers were secured with cyanoacrylate adhesive from Loctite. For the larger cylindrical formers the silk filaments at the ends were secured by a thin line of superglue running parallel to the long axis of the cylindrical former. This allows the removal of the composite material from the cylindrical former making a cut along the thin line of adhesive.

The composite material was formed either by painting a thin coat of either cyanoacrylate adhesive or concentrated regenerated fibroin solution on to the silk filaments. The regenerated fibroin solution was prepared by dissolving commercial degummed *Bombyx mori* fibroin powder in aqueous 63 M lithium bromide with gentle stirring at room temperature. The silk solution was then dialysed in 18-20 kDa MWCO Visking tubes with two changes for a total of 6 hours at 4 degrees-centigrade against aqueous 0.5M lithium bromide solution with the intention of allowing the protein to refold after dissolution in the concentrated lithium bromide. Thereafter water was removed from the fibroin solution by reverse dialysis against aqueous 40% aqueous—or dry powdered—polyethylene glycol (MW 15-20 kDa), pooling the partially concentrated fibroin after 12 hours-24 hours of dialysis to a fresh dialysis tube to obtain a final highly concentrated solution. Alternatively the dialysed silk fibroin solution was allowed to partially dry by exposing the sealed the dialysis bag to dry air. The matrix material was applied by painting the concentrated fibroin onto the silk filaments and allowed to dry. Thereafter the matrix was cross-linked by treatment with substantially dry formaldehyde gas by heating to 80-100 degrees centigrade for 5 minutes to 3 hours in a sealed vessel containing substantially dry paraformaldehyde. Unreacted formaldehyde was removed by heating the material to 100 degrees centigrade in a stream of air or by exhaustive washing.

Testing of the composite materials for mechanical strength was carried out by cutting silk acrylate strips made using the larger cylindrical formers as described below in Example 3. An Instron universal mechanical testing instrument fitted with pneumatic grips was used to test composite strips to failure in uniaxial tension parallel to the lay of the silk filaments.

Example 2

Demonstration of RGD Putative Integrin Binding Sites on *Antheraea* spp Heavy Chain Fibroins and their Location Adjacent to Turns The published sequences of silk proteins were searched on the TrEMBL and SwissPROT data bases for the well established cell binding sequence RGD and the putative cell binding sites PPSRN (SEQ ID NO: 1) and KNEED (SEQ ID NO: 2). The sequence triplet RGD is of considerable interest as it forms part of the mechanism used in multicellular organisms to stick many types of cells to the connective tissue framework of the body. The RGD triplet on the silk-like connective tissue protein fibronectin binds specifically to integrins. Integrins are a class of cell adhesion molecules. They are found intercalated into the lipid bilayer of the cell membrane with the fibronectin binding (RGD recognition) site protruding into the extracellular space. Thus the RGD recognition site of integrins is available to bind cells to the connective tissue framework via RGD triplets on fibronectin molecules.

The putative cell binding sites PPSRN (SEQ ID NO: 1) and KNEED (SEQ ID NO: 2) were absent from all silks examined. However, multiple copies of the triplet RGD were found in the glycine rich domains of three heavy chain fibroins of *Antheraea pemyi* (TrEMBL 076786), *A. yamamai* (TrEMBL Q964F4) and *A. militta* (Q8ISB3). There were 12 and 14 repeats respectively in the complete sequence of *A. pernyi* and *A. yamamai* and an even higher density of repeats (7) in the partial sequence of *A. militta*. The remarkably repetitive location of the RGD repeats is shown for *A. pernyii* in FIGS. 4(A-C). The RGD motif recurs in a constant location, in the glycine-rich repeat immediately separated by one polyalanine repeat before the sequence SAARRAGHDRAAGS (SEQ ID NO: 3) (sometimes truncated to RRAGHDRAAGS; SEQ ID NO: 4) or a closely similar sequence.

In all cases the RGD triplet immediately preceded the motif GGYG (SEQ ID NO: 5). *A. militta* differed from the two other *Antheraea* sp in having two RGD's instead of one in one of its glycine-rich domains.

The RGD triplet was absent from all other silk protein sequences examined with the exception of that for *Samia ricini* heavy chain fibroin which contained a single copy immediately preceding a YGSD (SEQ ID NO: 6) motif in a glycine-rich domain close to the end of this very long sequence.

Thus the cell-binding sequence RGD is found in multiple copies in the heavy chain fibroins of three *Antheraea* species.

We then sought to discover if the RGD sequence is present in locations within the silk molecule likely to be accessible to cell surface integrins. To seek an answer to this we first used RADAR (Expasy tools) to determine the consensus sequence for the repetitive glycine rich domains of *Antheraea pernyii* heavy chain fibroin (see FIG. 5).

This showed that the sequence GGYGXGDGGYGSDS (SEQ ID NO: 7) (where X=W or R) was well conserved within the glycine-rich domains. We then used a sophisticated secondary structure prediction tool, SCRATCH (Expasy tools) to determine the location of a putative turn within the consensus sequence (see FIG. 6), as previous research (Peng et al. 2004 in preparation) has shown that turns are present within silk molecules as part of a tertiary structure defined by the existence of antiparallel0-sheets. A turn in the *A. pernyi* consensus sequence was found to be centred on a glycine residue immediately adjacent to the RGD. As each RGD triplet in fibronectin are located immediately adjacent to a turn (Leahy, Hendrickson et al. 1992; Leahy, Aukhil et al. 1996). We conclude that the RGD in *Antheraea* silks is likely to be available for binding to integrins and is therefore likely to strongly promote cell adhesion to this silk.

Example 3

Tensile Data on *Antheraea pernyi* Cyanoacrylate Composite

|  | UTS (Mpa) | Strain to failure | Energy/kg (JKg) | Modulus (Mpa) |
|---|---|---|---|---|
| Average: | 31 | 0.150 | 1900 | 1000 |
| SD | 8.080 | 0.016 | 590 | 227 |

For comparison, the ultimate tensile stress of a typical-low alloy steel is in the region of 830 Mpa and a modulus of 200 Mpa but steel has a density of approximately 6 times that of the silk composite thus weight for weight this steel is less than 4 times as strong as the silk composite. The tensile data for the silk composite are comparable with that of that of two synthetic implantable materials (table 2).

TABLE 2

Tensile-data for wild silk-cyanoacrylate composite compared-with two synthetic implantable materials.

| Property | Poly-L-lactide | Poly ε caprolactone | *A.pernyi* acrylate composite |
|---|---|---|---|
| Ultimate tensile strength | 45 MPa | 22 MPa | 31 MPa |
| Ultimate extension | 3% | 500% | 16% |
| Initial modulus | 23 GPa | 0.4 GPa | 1 GPa |

---

The invention claimed is:

1. A surgically implantable device comprising a biocompatible composite material, wherein;
said biocompatible composite material comprises one or more silk elements,
said silk elements comprise at least one silk protein selected from the group of proteins consisting of wild silkworm silk proteins, recombinant wild silkworm silk proteins, and analogues thereof,
the protein sequence of said at least one silk protein comprises at least eight repeats of the triplet RGD, and
said one or more silk elements are embedded in a cross-linked fibroin or cross-linked casein protein matrix.

2. The surgically implantable device of claim 1, wherein at least some of the at least eight repeats of the triplet RGD are located immediately adjacent to turns or predicted turns of a structure of the silkworm silk protein.

3. The surgically implantable device of claim 1, wherein said at least one silk protein is from a silk worm selected from the group of silkworms consisting of *Antheraea yamamai* and *Antheraea militta*.

4. The surgically implantable device of claim 1, wherein the device is substantially cylindrical and the one or more silk elements are arranged longitudinally on a surface of the surgically implantable device.

5. The surgically implantable device of claim 1, wherein the device is substantially cylindrical and the one or more silk elements are arranged in a helical manner on the surface of the device.

6. The surgically implantable device of claim 1, wherein the device is substantially cylindrical and the one or more silk elements are arranged circumferentially on the surface of the device.

7. The surgically implantable device of claim 1, wherein the biocompatible material has been mineralized.

8. The surgically implantable device of claim 1, wherein the biocompatible material consists of a composite material comprising one or more silk fibers, twisted threads, rods, sheets or tubes in a cross-linked protein matrix.

9. The surgically implantable device of claim 8, wherein said silk fibers, twisted threads, rods, sheets or tubes are woven, braided, embroidered or knitted together.

10. The surgically implantable device of claim 1, wherein the device is an endoluminal device.

11. The surgically implantable device of claim 1, wherein the device is a suture.

12. The surgically implantable device of claim 1, wherein the device is a stent device.

13. The surgically implantable device of claim 1, wherein the device is an anastomosis device.

14. The surgically implantable device of claim 1, wherein the device is a sleeve to guide regenerating nerve cell processes.

15. The surgically implantable device of claim 3, wherein said silkworm is *Antheraea yamamai* and said at least one silk protein is SEQ ID NO: 9.

16. The surgically implantable device of claim 3, wherein said silkworm is *Antheraea militta* and said at least one silk protein is SEQ ID NO: 10.

17. The surgically implantable device of claim 1, wherein the cross-linked protein matrix is cross-linked fibroin.

18. The surgically implantable device of claim 9, wherein the cross-linked protein matrix is cross-linked fibroin.

19. The surgically implantable device of claim 12, wherein the cross-linked protein matrix is cross-linked fibroin.

20. The surgically implantable device of claim 13, wherein the cross-linked protein matrix is cross-linked fibroin.

* * * * *